US008586768B2

(12) United States Patent
Kanthasamy et al.

(10) Patent No.: US 8,586,768 B2
(45) Date of Patent: Nov. 19, 2013

(54) DESIGN, SYNTHESIS AND FUNCTIONAL CHARACTERIZATION OF ROTTLERIN ANALOGS

(75) Inventors: Anumantha G. Kanthasamy, Ames, IA (US); George A. Kraus, Ames, IA (US); Vellareddy Anantharam, Gilbert, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 454 days.

(21) Appl. No.: 12/945,180

(22) Filed: Nov. 12, 2010

(65) Prior Publication Data

US 2011/0112182 A1    May 12, 2011

Related U.S. Application Data

(60) Provisional application No. 61/260,676, filed on Nov. 12, 2009.

(51) Int. Cl.
*C07D 311/58* (2006.01)
*C07D 311/70* (2006.01)
*A61K 31/352* (2006.01)

(52) U.S. Cl.
USPC .......................................... 549/405; 514/456

(58) Field of Classification Search
USPC .......................................... 549/405; 514/456
See application file for complete search history.

(56) References Cited

U.S. PATENT DOCUMENTS 7,632,819 B1    12/2009    Kanthasamy

OTHER PUBLICATIONS

Anantharam, Vellareddy, "Development of Novel Neuroprotective Agents for Parkinson's Disease", [retrieved on Nov. 17, 2009], retrieved from: http://www.novoseek.com, National Institutes of Health, Aug. 11, 2008.
Anantharam, Vellareddy, "Development of Novel Neuroprotective Agents for Parkinson's Disease", Abstract [retrieved on Nov. 17, 2009], retrieved from http://www.researchgrantdatabase.com, Aug. 15, 2008.
Anantharam, V. et al., "Blockade of PKCdelta Proteolytic Activation by Loss of Function Mutants Rescues Mesencephalic Dopaminergic Neurons from Methylcyclopentadienyl Manganese Tricarbonyl (MMT)—Induced Apoptotic Cell Death", Ann. N.Y. Acad. Sci., 1035:271-289 (2004).
Anantharam, V. et al., "Caspase-3-Dependent Proteolytic Cleavage of Protein Kinase Cdelta is Essential for Oxidative Stress-Mediated Dopaminergic Cell Death after Exposure to Methylcyclopentadienyl Manganese Tricarbonyl", The Journal of Neuroscience, Mar. 1, 2002, 22(5):1738-1751.
Anantharam, Vellareddy, "Development of Novel Neuroprotective Agents for Parkinson?s Disease", National Institutes of Health 2008, Grant Description, http://www.novoseek.com/DocumentDetailAction.action?numdocs=0&filt . . . , 2 pages, printed from Internet Nov. 17, 2009.
Anantharam, Vellareddy, "Development of Novel Neuroprotective Agents for Parkinson?s Disease", Abstract, 1 page, http://www.researchgrantdatabase.com/g/1R43NS063422-Development . . . , printed from Internet Nov. 17, 2009.
Beal, M. Flint, "Mitochondria Take Center Stage in Aging and Neurodegeneration", Neurological Progress, 2005 American Neurological Association, pp. 495-505.
Dawson, Ted M., "Clinical Trials in Other Neurological Diseases", "Failures and Successes of Clinical Trials for Parkinson Disease Treatments", Retina, 2005, The Journal of Retinol and Vitreous Diseases, 25(8 Suppl): p. S75-S77.
Dawson, Ted M., "Molecular Pathways of Neurodegeneration in Parkinson's Disease", Science, vol. 302, Oct. 31, 2003, pp. 819-822.
Dhib-Jalbut, Suhayl et al. "Neurodegeneration and neuroprotection in multiple sclerosis and other neurodegenerative diseases", Journal of Neuroimmunology, 176 (2006) 198-215.
Di Monte, Donato A., et al., "Environmental Factors in Parkinson's Disease", NeuroToxicology, 23 (2002) 487-502.
Forman, Mark S. et al., "Neurodegenerative diseases: a decade of discoveries paves the way for therapeutic breakthroughs", Nature Medicine, vol. 10, No. 10, Oct. 2004, pp. 1055-1063.
Gabison, Yoram, "Israeli company develops drug proven to slow progression of Parkinson's" HAARETZ.com, Home News, published Aug. 27, 2008, 2 pages, http://www.haaretz.com/hasen/pages/ShArt.jhtml?itemNo=1015506 (accessed Mar. 9, 2009).
Greenamyre, J. Timothy et al., "Parkinson's—Divergent Causes, Convergent Mechanisms", Biomedicine, Science, vol. 304, May 21, 2004, pp. 1120-1122.
Jenner, Peter et al., "The pathogenesis of cell death in Parkinson's disease", Neurology, 2006. 66 (10 Suppl 4): p. S24-36.
Kanthasamy, Anumantha G. et al., "A novel peptide inhibitor targeted to caspase-3 cleavage site of a proapoptotic kinase protein kinase C delta (PKCdelta) protects against dopaminergic neuronal degeneration in Parkinson's disease models", Free Radical Biology & Medicine, 2006. 41(10): p. 1578-1589.
Kanthasamy, Anumantha G. et al., "Role of Proteolytic Activation of Protein Kinase Cdelta in Oxidative Stress-Induced Apoptosis", Antioxidants & Redox Signaling, 2003. 5(5): p. 609-620.
Kaul, Siddharth et al., "Tyrosine Phosphorylation Regulates the Proteolytic Activation of Protein Kinase Cdelta in Dopaminergic Neuronal Cells", The Journal of Biological Chemistry, Aug. 2005, 280(31): p. 28721-28730.
Kaul, Siddharth et al., "Wild-type alpha-synuclein interacts with pro-apoptotic proteins PKCdelta and BAD to protect dopaminergic neuronal cells against MPP+-induced apoptotic cell death", Molecular Brain Research, 2005. 139(1): p. 137-152.

(Continued)

*Primary Examiner* — Bernard Dentz
(74) *Attorney, Agent, or Firm* — McKee, Voorhees & Sease, P.L.C.

(57) ABSTRACT

A method of synthesizing rottlerin analogs is described. The synthesis methods described are the first known method of synthesizing rottlerin analogs from commercially-available materials to produce cost effective analogs. Rottlerin analog structures made by the synthesis methods and methods of use for treating a neurological or inflammatory response mediated by protein kinase C (PKC) are further described.

9 Claims, 16 Drawing Sheets

(56) References Cited

OTHER PUBLICATIONS

Kitazawa, M. et al., "Dieldrin induces apoptosis by promoting caspase-3-dependent proteolytic cleavage of protein kinase Cdelta in dopaminergic cells: relevance to oxidative stress and dopaminergic degeneration", Neuroscience, 2003. 119(4): p. 945-957.

Lai, Justine Y.Q. et al., "Preparation of Kinase-Biased Compounds in the Search for Lead Inhibitors of Kinase Targets", Medicinal Research Reviews, vol. 25, No. 3, pp. 310-330, 2005.

Latchoumycandane, C., et al., "Protein Kinase Cdelta is a Key Downstream Mediator of Manganese-Induced Apoptosis in Dopaminergic Neuronal Cells", Journal of Pharmacology and Experimental Therapeutics, 2005. 313(1): p. 46-55.

LeWitt, Peter A. et al., "Protection Against Parkinson's Disease Progression: Clinical Experience", Neurotherapeutics: The Journal of the American Society for Experimental NeuroTherapeutics, 2008. 5(2): p. 210-225.

Moore, Darren J. et al., "Molecular Pathophysiology of Parkinson's Disease", Annu. Rev. Neurosci., 2005. 28: p. 57-87.

Perier, Celine et al., "Two molecular pathways initiate mitochondria-dependent dopaminergic neurodegeneration in experimental Parkinson's disease", Proc. Natl. Acad. Sci. USA, May 8, 2007, 104(19): p. 8161-8166.

Scheife, Richard T. et al., "Impact of Parkinson's disease and its pharmacologic treatment on quality of life and economic outcomes", Am. J. Health-Syst. Pharm., May 15, 2000, 57(10): p. 953-962.

Solodukhin, Alexander S. et al., "Two-Dimensional Crystal Structures of Protein Kinase C-delta, Its Regulatory Domain, and the Enzyme Complexed with Myelin Basic Protein", Biophysical Journal, vol. 82, May 2002, pp. 2700-2708.

Sun, Faneng et al., "Proteasome inhibitor MG-132 induces dopaminergic degeneration in cell culture and animal models", NeuroToxicology, 2006. 27(5): p. 807-815.

Yang, Yongjie et al., "Suppression of caspase-3-dependent proteolytic activation of protein kinase C delta by small interfering RNA prevents MPP+-induced dopaminergic degeneration", Mol. Cell. Neurosci., 2004. 25(3): p. 406-421.

Zhang, Danhui et al., "Neuroprotective Effect of Protein Kinase Cdelta Inhibitor Rottlerin in Cell Culture and Animal Models of Parkinson's Disease", J. Pharmacol. Exp. Ther., 2007. http://jpet,aspetjournals.org/cgi/content/full/322/3/913, Printed Internet Aug. 10, 2009, 13 pages.

Zhang, Chao et al., "Scaffold-based design of kinase inhibitors for cancer therapy", Current Opinion in Genetics & Development, 2010, 20:79-86.

Kanthasamy, Anumantha, "Grow Iowa Value Fund", Board of Regents memo, Jul. 15, 2009. 8 pages.

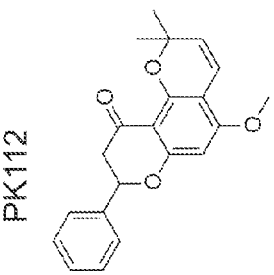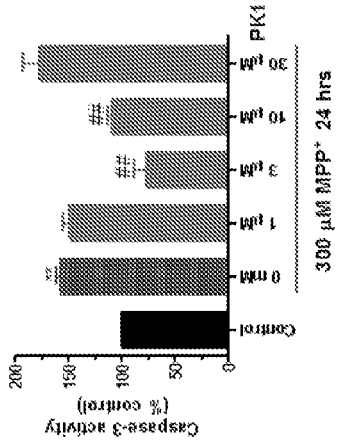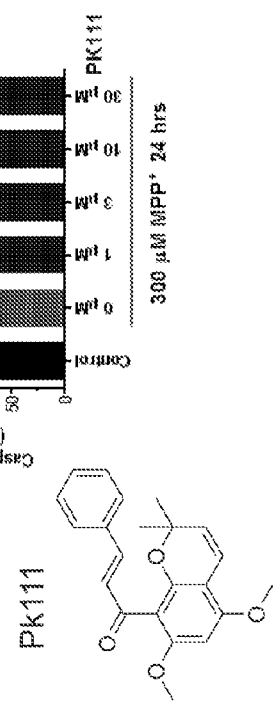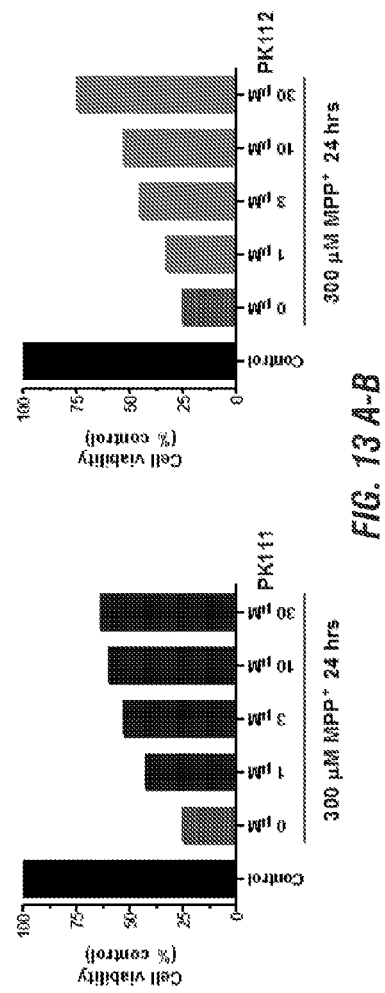
FIG. 13 A-B

DESIGN, SYNTHESIS AND FUNCTIONAL CHARACTERIZATION OF ROTTLERIN ANALOGS

CROSS-REFERENCE TO RELATED APPLICATIONS

This application is a nonprovisional application of U.S. Provisional Application No. 61/260,676, filed Nov. 12, 2009, which is herein incorporated by reference in its entirety.

GRANT REFERENCE

This invention was made with government support under Grant Nos. 1R43NS063422-01 and R01 NS38644 funded by National Institute of Health (NIH). The United States government has certain rights in this invention.

FIELD OF THE INVENTION

This invention relates to methods of synthesizing small molecule kinase inhibitors of PKCδ, namely rottlerin analogs, providing an efficient and cost-effective way to produce rottlerin analogs from commercial materials. The invention further relates to rottlerin analogs synthesized from the methods described herein.

BACKGROUND OF THE INVENTION

Various neurodegenerative disorders are characterized by selective degeneration of nigral dopaminergic neurons in the brain, including Parkinson's disease (PD). PD is the second most common neurodegenerative disorder after Alzheimer disease and affects more than 1.5 million people in the U.S. with approximately 50,000 to 60,000 new cases diagnosed each year. The disease is characterized by the cardinal motor symptoms of rigidity, bradykinesia, tremors and postural instability. Existing treatment options for neurodegenerative disorders fail to prevent the progression of the degeneration. As a result, development of neuroprotective agents to delay progression of the disease is needed. The apoptotic cell death pathway mediated by protein kinase C is a viable treatment pathway.

Protein kinase C (PKC) belongs to a family of serine threonine protein kinases. To date, twelve isoforms in the PKC subfamily have been identified (Kanthasamy et al., Antioxidants & Redox Signaling, 5: 609-620, 2003). One such isoform is protein kinase C delta (PKCδ) (Martelli et al., Eur. J. Histochem., 48(1):89-94, 2004).

PKCδ was originally discovered by Gschwendt et al. (Biochem. Biophys. Res. Commun., 137: 766-74, 1986) and cloned from a rat brain cDNA library the following year (Kurkinen et al., Gene 242: 115-23, 2000; Ono et al., Identification of three additional members of rat protein kinase C family: delta-, epsilon- and zeta-subspecies. FEBS Lett., 226: 125-8, 1987). The PKCδ gene is localized on human chromosome 3 (Huppi et al., Assignment of the protein kinase C delta polypeptide gene (PKCδ) to human chromosome 3 and mouse chromosome 14. Genomics 19: 161-2, 1994), rat chromosome 16 (Kurkinen et al., Genomic structure and chromosomal localization of the rat protein kinase C delta gene. Gene 242: 115-23, 2000), and mouse chromosome 14 (Huppi et al., Assignment of the protein kinase C delta polypeptide gene (PKCδ) to human chromosome 3 and mouse chromosome 14. Genomics. 19: 161-62, 1994).

Rottlerin exhibits biological activity, including selectively inhibiting protein kinase C delta (PKCδ). Rottlerin is a natural product that is isolated from the seeds of the fruit *Mallotus philippinensis*, most commonly produced in India, Philippines, Southeast Asia, and Australia. The IUPAC name for rottlerin is (E)-1-[6-[(3-acetyl-2,4,6-trihydroxy-5-methylphenyl)methyl]-5,7-dihydroxy-2,2-dimethylchromen-8-yl]-3-phenylprop-2-en-1-one. The molecular formula for the structure is $C_{30}H_{28}O_8$ and the structure has a molecular weight of 516.53852 g/mol. The chemical structure of rottlerin is shown below:

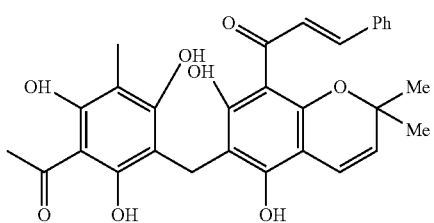 [SMILES: CC(=O)c1c(O)c(C)c(O)c(Cc2c(O)c3c(c(C(=O)/C=C/c4ccccc4)c2O)OC(C)(C)C=C3)c1O]

Rottlerin selectively inhibits PKCδ with an $IC_{50}$ of 3-6 μM. Although rottlerin is widely used as a specific inhibitor of PKCδ (McCormack et al., Neurobiol. Dis., 10(2): 119-27, 2002; Kanthasamy et al., Brain Res., 759(1): 1-8, 1997; Przedborski et al., Proc. Natl. Acad. Sci., 93(10): 4565-71, 1996), rottlerin has also been shown to inhibit PRAK, MAP kinases, and CAMKII kinases at higher concentrations (Turmel et al., Mov. Disord., 16(2): 185-9, 2001; Jackson-Lewis et al., Neurodegeneration, 4(3): 257-69, 1995).

Synthesis of rottlerin has not been reported. No studies of the scope and limitations of the preparation of rottlerin and/or any synthetic analogs have been reported. Similarly, there is a lack of detailed studies of the molecular mechanism of action of rottlerin; it is unknown what segments of the rottlerin structure are biologically active. However, documented uses of the rottlerin structure are known (see e.g., Kanthasamy et al. U.S. patent application Ser. Nos. 11/479,173 and 61/240,906) but are significantly restricted due to the limited natural abundance of the substance. Due to such limited abundance, rottlerin is cost prohibitive for use as a drug therapy, despite its identified beneficial actions as a PKCδ inhibitor. Accordingly, methods of rottlerin synthesis in large quantities are desirable in order to obtain sufficient quantities of the analog for future studies. Further, synthetic rottlerin that are PKCδ inhibitors with better selectivity and more affinity are desirable and an objective of the present invention.

Accordingly, it is an objective of the present invention to develop methods and means of synthesizing PKCδ inhibitor analogs from the rottlerin base structure.

It is a further objective of the present invention to develop rottlerin analogs having simplified chemical structures in order to identify analogs with enhanced biological activity compared to natural rottlerin.

It is a further objective of the present invention to develop methods of rottlerin analog synthesis from commercially-available materials comprising minimal synthesis steps, namely four or fewer synthesis steps.

The method and means of accomplishing each of the above objectives as well as others will become apparent from the detailed description of the invention which follows hereafter.

SUMMARY OF THE INVENTION

The present invention describes methods of rottlerin analog synthesis and compounds produced according to the methods, namely analog synthesis, resulting in structures with maintained or increased biological PKCδ inhibitory activity and effectiveness over natural rottlerin. The compounds are produced from cost-effective and commercially-available products and preferably involve four or fewer synthesis steps. The methods according to the invention result in analogs having simpler structures than natural rottlerin.

Rottlerin analogs are disclosed according to the invention comprising the following formula:

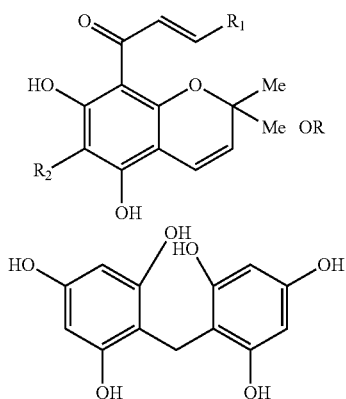

wherein R1 is selected from the group consisting of Ph (phenyl), phenol, CH$_2$Ph, CH$_2$-heterocycle and a substituted phenyl and wherein R2 is selected from the group consisting of halogens, H, OH, and benzyl, wherein said analog has biological PKCδ inhibitory potency exceeding natural rottlerin.

According to further embodiments of the invention, rottlerin analogs are disclosed comprising one of the following formulas:

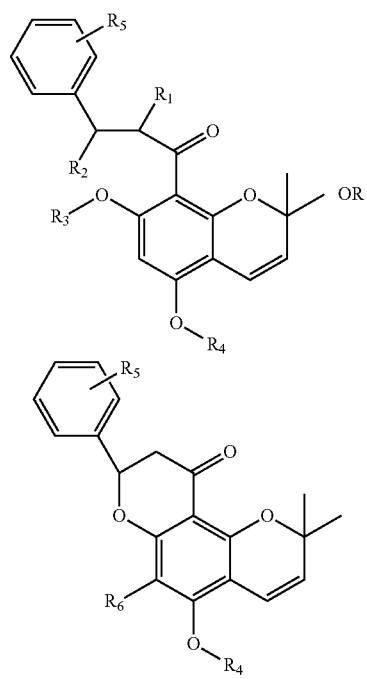

wherein R1 and R2 are selected from the group consisting of H and CH$_2$, wherein R3 and R4 are selected from the group consisting of H and alkyl, wherein R5 is selected from the group consisting of H, halogen, alkoxy and amino, wherein R6 is selected from the group consisting of H, hydroxy alkyl, (3-acetyl-5-methyl-2,4,6-trihydroxybenzyl), 2,4,6-trihydroxybenzyl and (3-acetyl-2,4,6-trihydroxybenzyl), and wherein said analog has biological PKCδ inhibitory potency exceeding natural rottlerin.

A further embodiment of the invention is a method for synthesizing rottlerin analogs comprising reacting a phloroglucinol starting material with a hydrocarbon and a heterocyclic compound to form a quinone intermediate; undergoing an aldol condensation reaction with said quinone intermediate to add an aromatic ring to said intermediate; and coupling a double bond to an oxygen-containing ring structure of the analog.

A method of treating a neurological or inflammatory response mediated by protein kinase C (PKC) in an animal is further embodied by the invention and comprises administering to an animal in need thereof, an effective amount of a rottlerin analog according to the invention. According to a preferred embodiment, the neurological or inflammatory response is Parkinson's disease.

A method for treating Parkinson's disease comprising modulating the activity of protein kinase Cδ (PKCδ) by administering a rottlerin analog according to the invention is further disclosed.

A pharmaceutical composition for treating a neurological or inflammatory response mediated by protein kinase C (PKC) in an animal is disclosed according to an embodiment of the invention. The pharmaceutical composition comprises a rottlerin analog according to the invention and a pharmaceutically acceptable carrier.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The invention can be more fully understood from the following detailed description and the accompanying figures.

FIGS. 13A-B illustrate the neuroprotective effect of PK analogs in cell culture models of Parkinson's disease.

DETAILED DESCRIPTION OF THE PREFERRED EMBODIMENT

Figure 1:
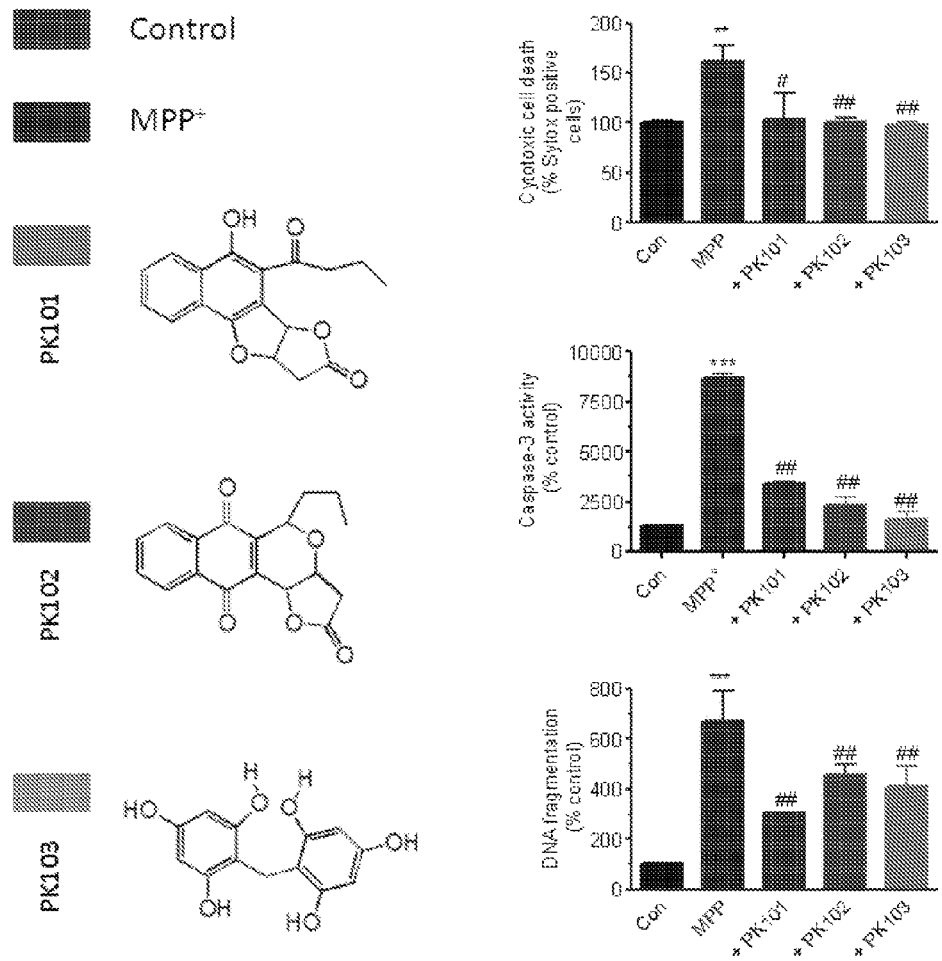
FIG. 1 illustrates the effect of first generation PK analogs on Parkinsonian neurotoxicant MPP+-induced caspase-3 activation, cytotoxic and apoptotic cell death. The effect of blockage of MPP+-induced cytotoxicity in N27 dopaminergic cell model co-treated with 3 μM PK101, PK102, and PK103 as PKCδ inhibitors is shown.

The embodiments of this invention can vary and are understood by those skilled in the art. It is further to be understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein.

The term "alkenyl," as used herein or represented in figures of analogs according to the invention, refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted.

The term "alkyl," as used herein or represented in figures of analogs according to the invention, refers to a saturated aliphatic hydrocarbon moiety including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted.

The term "alkynyl," as used herein or represented in figures of analogs according to the invention, refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted.

The term "amino," as used herein or represented in figures of analogs according to the invention, refers to the moiety —NR'R' wherein each R' is, independently, hydrogen, amino, hydroxyl, alkoxyl, alkyl, aryl, cycloalkyl, heterocycloalkyl, heteroaryl, alkyl heteroaryl or the like. The two R' groups may themselves be linked to form a ring. The R' groups may themselves be further substituted, which is specifically contemplated under the term "amino".

The term "analog," as used herein, refers to a compound resulting from substitution, replacement, or deletion of various organic or inorganic groups and/or hydrogen atoms from a parent compound, such as rottlerin.

The term "aryl" or "aromatic ring," as used herein or represented in figures of analogs according to the invention, refers to an aromatic carbocyclic moiety. "Aryl" may be exemplified by phenyl. The aryl group may be substituted or unsubstituted. Substituents may also be themselves substituted. When substituted, the substituent group is preferably but not limited to alkoxyl, heteroaryl, acyl, carboxyl, carbonylamino, nitro, amino, cyano, halogen, or hydroxyl.

The term "carboxyl," as used herein or represented in figures of analogs according to the invention, refers to the group —C(=O)O—R. The term "carbonyl," as used herein or represented in figures of analogs according to the invention, refers to the group —C(O)R. The term "carbonylamino," as used herein or represented in figures of analogs according to the invention, refers to the group —C(O)NR'R'.

As used herein, including description and/or figures of analogs according to the invention, the term "halogen" refers to the nonmetal elements from Group 17 of the periodic table (IUPAC), including fluorine (F), chlorine (Cl), bromine (Br), and iodine (I).

The term "hydroxy" or "hydroxyl," as used herein or represented in figures of analogs according to the invention, means a chemical entity that consists of —OH. Alcohols contain hydroxy groups. Hydroxy groups may be free or protected. An alternative name for hydroxyl is alcohol.

As used herein, the term "inhibiting" or "inhibits" refers to the ability to reduce or decrease a level, an amount, an activity, the severity of a disease, disorder, condition or symptom and the like, e.g. of mRNA or protein or activity, for example, as compared to a control.

The terms "protein kinase C delta," "PKC-delta," "PKCdelta," "PKCd," "PKCδ" or "PKC delta" may be used interchangeably herein.

As used herein, "PKCδ activity" refers to an activity exerted by a native or wild type PKCδ protein, polypeptide or portion thereof as determined in vivo, ex vivo or in vitro, according to standard techniques. PKCδ activity may include any one of the following activities: (1) modulation of the subcellular location of the PKCδ protein, e.g. the translocation of the PKCδ from one subcellular location to another, for example, to the plasma membrane from a different subcellular location, such as the nucleus or cytosol, (2) modulation of the phosphorylation of the PKCδ protein, (3) modulation of the PKCδ protein to phosphorylate a known PKCδ substrate, (4) modulation of the expression level of the PKCδ mRNA or protein, (5) modulation of the production of pro-inflammatory substances in a microglial cell such as an activated microglial cell, (6) modulation of the release of pro-inflammatory substances from an activated microglial cell, (7) modulation of the production of pro-inflammatory substances in a macrophage or mononuclear phagocyte such as an activated macrophage or mononuclear phagocyte, (8) modulation of the release of pro-inflammatory substances from an activated macrophage or mononuclear phagocyte, (9) modulation of neuroinflammation, (10) modulation of the production of anti-inflammatory substances in a mononuclear phagocyte, macrophage, or microglial cell, (11) modulation of the release of anti-inflammatory substances in a mononuclear phagocyte, macrophage, or microglial cell, (12) modulation of the production of trophic factors from other brain cells such as astrocytes, macrophages or mononuclear phagocytes, (13) modulation of enzymes involved in microglial, mononuclear phagocyte, or macrophage activation, for example, that participate in the production or regulation of pro-inflammatory substances, such as NADPH oxidase and inducible nitric oxide synthase (inos) or isoforms or components of these enzymes, e.g. p67phox, gp91 phox, p47phox and the like, and/or (14) any combination thereof. As used herein, depending on the context in which it is used, modulation refers to an increase or decrease in an activity, amount or level, or a change in the type or kind of activity present as compared to a control. Preferably the PKCδ inhibitor decreases or inhibits expression of and/or an activity of a native or wild type PKCδ, for example, as compared to a control.

As used herein, the term "PKCδ inhibitor" includes any compound capable of down-regulating, decreasing, reducing, suppressing or inactivating the amount and/or activity of PKCδ. Generally, said inhibitors may be proteins, oligo- and polypeptides, polynucleotides, genes, lipid, polysaccharide, drugs, small chemical molecules, or other chemical moieties. Inhibitors for use with the invention may function to inhibit PKCδ by any number of ways, including decreasing PKCδ mRNA or protein levels or by blocking the activation of PKCδ or its activity, for example, through inhibiting or decreasing proteolytic cleavage of PKCδ, e.g. using a PKCδ peptide cleavage inhibitor, and/or inhibiting the phosphorylation of PKCδ, e.g. at tyrosine residues including those located at positions Y155, Y187, Y313, Y334 and Y514 at threonine and serine including those located at position T511 and S645 and 664 in human PKCδ protein. Compounds that decrease activity of PKCδ downstream of PKCδ in its pathway, such as kinases downstream of PKCδ, and/or decrease products or activity of PKCδ targets, for example, PP2A and TH, or decrease activity upstream of PKCδ are also within the scope of PKCδ inhibitors of the present invention.

The term "ring" as used herein or represented in figures of analogs according to the invention, means a collection of member atoms that are cyclic. Rings may be carbocyclic, aromatic, heterocyclic, or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

Rottlerin Analogs

According to the invention, small molecule kinase inhibitors of PKCδ are provided. The kinase inhibitors of PKCδ according to the invention are analogs of the natural substance rottlerin. Remarkably, the Inventors have found that rottlerin analogs provide greater neuroprotective efficacy and higher therapeutic index compared to the natural substance rottlerin.

The rottlerin structure has a left and right side of the structure, wherein the left side contains a benzyl ring with an acetyl group and the right side contains a two ring structure with a dimethyl group and the carbonyl double bonded to a phenyl group. Analysis of this natural rottlerin structure shows that modifications to the right-hand structure most greatly affect the biological activity of the structure. According to the invention, rottlerin analogs preferably have modifications to the quinine structure of the rottlerin skeleton.

As described according to the invention, synthetic rottlerin analogs are developed. The analogs described herein according to the invention, may be further understood by one skilled in the art to be structural analogs. Further, such analogs may be further described and understood by those skilled in the art to be chemical analogs, as the rottlerin analog compounds have at least one atom, functional group, or substructure that is replaced with different atoms, groups, or substructures. According to the invention, despite the chemical similarity of the rottlerin analogs to the natural substance rottlerin, the analogs are not necessarily functional analogs, as they demonstrate different physical and chemical properties. Namely, the rottlerin analogs, according to an embodiment of the invention, demonstrate maintained or improved biological PKCδ inhibitory activity over the natural substance rottlerin, as set forth herein the description of the invention.

Rottlerin analogs according to an embodiment of the invention have the following general formula:

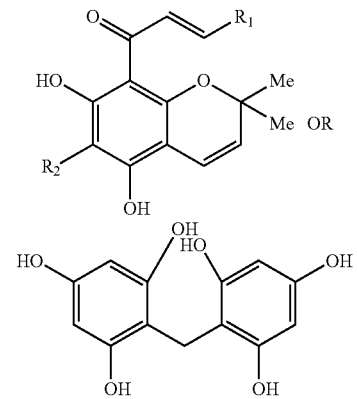

wherein R1 is selected from the group consisting of Ph (phenyl), phenol, $CH_2Ph$, $CH_2$-heterocycle and a substituted phenyl and wherein R2 is selected from the group consisting of halogens, H, OH, and benzyl. Suitable examples of substituted phenyls may include dihydroxy phenyl, hydroxy phenol, methoxyl hydroxy phenyl, halo-phenyl, amino-phenyl and the like.

Further embodiments of the invention include the analog wherein an R1 group is phenyl. According to a further embodiment of the invention, the analog has an R2 that is a halogen. Suitable halogen moieties include fluoro, chloro, bromo, or iodo. The analog according to an embodiment of the invention may further have an R1 group that is a dihydroxy phenyl and an R2 group that is a H. The analog according to a still further embodiment of the invention may have an R1 group that is a halo-phenyl and an R2 group that is a H.

According to a further embodiment, the phenol groups of the analog are replaced with methoxy groups. Methoxy protected phenols, or methyl ethers, provide analogs having decreased reactivity according to the invention.

Rottlerin analogs according to a further embodiment of the invention have the following general formula:

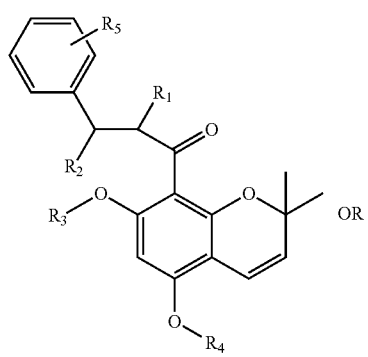

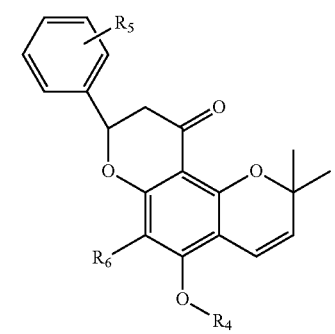

wherein R1 and R2 are selected from the group consisting of H and CH$_2$, wherein R3 and R4 are selected from the group consisting of H and alkyl, wherein R5 is selected from the group consisting of H, halogen, alkoxy and amino, wherein R6 is selected from the group consisting of H, hydroxy alkyl, (3-acetyl-5-methyl-2,4,6-trihydroxybenzyl), 2,4,6-thrihydroxybenzyl and (3-acetyl-2,4,6-trihydroxybenzyl), and wherein said analog has biological PKCδ inhibitory potency exceeding natural rottlerin. According to a further embodiment of the invention, the R3 and R4 groups of the analog are alkyl groups having between 1 and 5 carbons. R1 and R2 may be further selected from the group consisting of H and H double bond.

The terms "alkyl," "alkenyl," and "alkynyl" as used herein as a group or a part of a group respectively mean alkyl, alkenyl, and alkynyl that the group is of a straight chain, branched chain, or cyclic type or a type of a combination thereof unless otherwise specified. Further, for example, C1-6 as a group or a part of a group means that the number of carbon atoms in the group is 1 to 6.

According to further embodiments of the invention, scaffold-based design, compound modification using linkers and/or allosteroid side inhibition are used to generate additional rottlerin analogs according to the following general formulas:

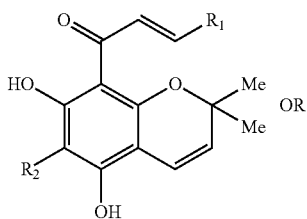

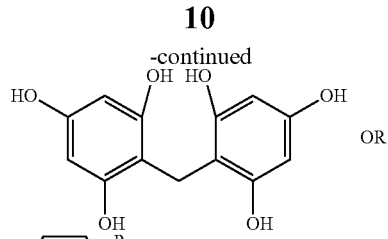

According to an embodiment of the invention, scaffold-based design is a powerful and efficient strategy for rapid generation of novel drug candidates to support a comprehensive strategy for therapeutic intervention. Scaffold paradigm in drug design includes an integrated drug discovery paradigm that starts with smaller molecular starting points, termed scaffolds, and incorporates X-ray crystallography at the outset of the project. The modular, anchor-and-grow nature of scaffold-based design is particularly suited as a tool to explore different mechanisms of inhibition. Scaffold-based design and implementation of these methods results in novel, potent and specific drug candidates (Zhang et al., 2010, Lai et al., 2005).

According to the invention, rottlerin analogs and its kinase inhibitor specificity is not dictated solely by the primary intended target, but rather by comparison to the entire spectrum of molecular recognition patterns in the kinome (Fabian et al., 2005). Scaffold-based design offers an effective means of exploiting shape and chemical differences among different kinases for the rapid generation of candidate inhibitors with desired target inhibition profiles. With this approach, selective targeting of particular kinase conformations can also be achieved by small molecule inhibitors, and this should enable the development of more specific therapeutic agents (Zhang et al., 2010, Lai et al., 2005).

One skilled in the art to which the invention pertains shall appreciate that scaffold-based drug design based upon the structure of lead PK analogs, including for example, PK103, PK202 and PK302, may be used to identify novel, more potent and highly specific inhibitor against our therapeutic target PKCδ whose X-ray crystallography structure is available (Solodukhin et al., 2002).

According to a further embodiment of the invention, compound modification using linkers generate additional rottlerin analogs according to the invention. According to an embodiment, a linker is used to add an additional functional group to an analog according to the invention to improve the analog's properties, such as pharmacokinetic properties over the unmodified analog.

Linkers may be utilized according to an embodiment of the invention to form derivative rottlerin analogs according to the invention. A derivative is referring to an analog according to the invention with a replacement of one or more atom with another atom or group of atoms based on the attachment of a linker to the analog according to the invention. However, depending on the type of modification and linker utilized, a different synthesis pathway may be necessary.

According to a further embodiment of the invention, allosteroid side inhibition is used to generate additional rottlerin analogs according to the invention.

One skilled in the art shall appreciated based on the disclosure of the present invention, that the functional groups identified in the structures of the rottlerin analogs may be further optionally substituted to provide enhanced biological properties. For example, "optionally substituted" as referred to for an alkyl group means that one or more hydrogen atoms on the alkyl group are optionally substituted by one or more substituents, which may be the same or different. It will be apparent to a person having ordinary skill in the art that the maximum number of substituents may be determined depending upon the number of substitutable hydrogen atoms on the alkyl group, which is true of alkenyl and alkynyl groups.

According to the present invention, the synthesized rottlerin analogs have maintained or enhanced biological properties over rottlerin, resulting in an unexpected benefit. According to an embodiment of the invention, the analogs can be used for treating, ameliorating, or preventing neurological and/or inflammatory responses, including for example Parkinson's disease. It is highly unexpected that significant modifications to a natural substance's structure, such as rottlerin, would result in enhanced biological activity. Rather, one skilled in the art would expect the biological activity to be diminished when the structure is significantly minimized and simplified.

According to an embodiment of the present invention, the synthesized rottlerin analogs have bioavailability to effectively cross the blood brain barrier. The analogs provide sufficient bioavailability for oral administration and thereafter demonstrate effectively crossing the blood brain barrier in order to exert the neuroprotective effects according to methods of treatment of the present invention.

Synthesis of Rottlerin Analogs

The present invention overcomes the limitations of a lack of any description of rottlerin synthesis and the molecular mechanism of action of rottlerin. According to an embodiment of the invention, methods of synthesis for simplified rottlerin analogs are provided. Remarkably, the Inventors have found identified a preferred synthesis route for the rottlerin analogs that involves four or fewer steps, generating the structural analogs from commercially-available materials to produce a cost-effective structural analog of rottlerin. The methods of the invention may contain four or fewer steps as a result of the ability to identify the particular structural groups or the rottlerin structure having significant effect on biological activity, as described herein.

The methods of synthesizing rottlerin analogs described according to the present invention make various modifications to the quinine structure of the rottlerin skeleton. According to one embodiment, analogs of the present invention preferably contain a double bond in the oxygen-containing ring of the compound to enhance biological activity. According to another embodiment, analogs of the present invention preferably contain a two ring structure having a dimethyl group. According to a still further embodiment of the invention, analogs of the present invention preferably contain a carbonyl double-bonded to a phenyl group. Maintaining the presence of these preferred groups provides a base analog structure for synthesis according to the methods of the present invention.

Additional substitutions, additions and modifications to the analog structure described herein may be contemplated and are encompassed by the scope of the present invention, as one of ordinary skill in the art would be able to determine based on the disclosure of the present invention.

Synthesis of rottlerin analogs according to the invention involves several steps, including beginning with the commercially-available material phloroglucinol (phloroglucinol dehydrate, $C_6H_6O_3$). As one skilled in the art will ascertain and appreciate, alternative commercially-available materials may be utilized, including for example, acetyl phloroglucinol or other derivatives of phloroglucinol. Alternatively, structurally similar aromatics may be utilized according to the methods of the present invention.

The first synthesis step is the interaction with the phloroglucinol starting material with isoprene and dioxane. 1,4-dioxane (dioxane) or a structurally similar heterocyclic organic compound may be utilized with isoprene (also referred to as isoterpene, 2-methyl-1,3-butadiene, $CH_2=C(CH_3)CH=CH_2$) or a similar hydrocarbon according to the methods of the invention. This first reaction introduces the oxygen-containing ring structure to the rottlerin analog. As one of ordinary skill in the art may recognize, the starting material may be reacted with a material that is functionally capable of adding the oxygen-containing ring structure to the starting material. Such alternative materials and reagents are well known in the art and can be readily determined as suitable for this purpose.

According to an embodiment of the invention, isoprene and dioxane are preferred compounds to introduce an oxygen-containing ring structure to the rottlerin analog. The starting material is reacted with the isoprene and dioxane or other suitable reagents for a time period sufficient for this chemical reaction to occur, which will generally range from about 18-24 hours. Preferably this addition occurs at an elevated temperature, for example, 90° C. As one skilled in the art may recognize, a catalyst (such as a solid acid catalyst) may be utilized for the reaction.

The synthesis of analogs according to the invention further includes the addition of a cinnamoyl group. According to the preferred synthesis steps of the invention, the addition occurs through a Friedel-Crafts acylation and then an aldol condensation with an aromatic aldehyde, such as for example a benzaldehyde.

According to a preferred embodiment of the invention, this step is completed in a two-step process to generate increased yields of the novel rottlerin analog intermediates. The steps include dissolving the intermediate in acetic acid (AcOH) before adding the phenyl group in the second synthesis step.

As one of ordinary skill in the art may recognize the intermediate with the oxygen-containing ring may be reacted with a material that is functionally capable of adding the carbonyl with the double bond to the phenyl group structure to the intermediate analog. These alternative materials and reagents are well known in the art and can be readily determined as suitable for this purpose. According to an embodiment of the invention, the preferred compounds are acetic acid, a phenyl group (PhCHO) with potassium hydroxide and alcohol. The starting material is reacted with the reagents or other suitable reagents for a time period sufficient for this chemical reaction to occur to add the carbonyl with the double bond to the phenyl group.

According to an embodiment of the invention, a double bond to the oxygen-containing ring of the rottlerin analog structure is added. According to a preferred embodiment of the invention, the reagent DDQ is added with benzene to add a double bond to the structure. One of ordinary skill in the art to which the invention pertains may recognize the intermediate with the oxygen-containing ring and carbonyl with the double bond to the phenyl group may be reacted with a material that is functionally capable of adding the double bond to the oxygen-containing ring of the intermediate analog. These alternative materials and reagents are well known in the art and can be readily determined as suitable for this purpose. According to an embodiment of the invention, preferred compounds are DDQ and benzene. The intermediates are reacted with the DDQ and benzene or other suitable reagents for a time period sufficient for this chemical reaction to occur to add the double bond to the oxygen-containing ring, preferably at least 12 hours at a temperature of about 80° C.

Temperatures and times for the reactions described above are not considered critical and may be modified by a person of ordinary skill in the art, although it has been found desirable for the reactions of the various synthesis steps to occur at or above room temperature, as preferably identified for each synthesis step. Pressure does not appear to be a controlling factor as atmospheric pressure works satisfactorily. The reactions are preferably employed in an inert atmosphere.

These reactions are further described and shown in the Examples. According to a further preferred embodiment of the invention the steps of the synthesis of the rottlerin analogs are performed in the sequence of identified synthesis steps. However, one skilled in the art of chemical synthesis may be able to modify the sequence of the synthesis steps, which is incorporated in the scope of the present invention.

According to additional embodiments of the invention, additional synthesis steps may be employed to add additional functional groups to the analog. For example, numerous substitutions may be contemplated by one of ordinary skill in the art at the phenyl group and on the benzene ring between the two hydroxyl groups, while maintaining or exceeding the desired biological activity of rottlerin.

Treatment using Rottlerin Analogs

According to the invention, rottlerin analogs are used for inhibiting human kinases, namely protein kinase C and more preferably PKCδ. The present invention relates to therapeutic methods and compositions for treatment of a disease, disorder, or condition associated with protein kinase C and more preferably PKCδ.

According to an embodiment of the invention, rottlerin analogs are used for treating, ameliorating, or preventing neurological and/or inflammatory responses, including for example Parkinson's disease. Accordingly, the invention provides for treatment or prevention of certain neurological and/or inflammatory responses by administration of a therapeutically effective amount of a rottlerin analog according to the invention or compound derived therefrom.

Methods for treating a neurological or inflammatory response mediated by protein kinase C (PKC) in an animal are disclosed. According to an embodiment of the invention, an animal in need of treatment for a neurological or inflammatory response mediated by protein kinase C (PKC) is administered an effective amount of a rottlerin analog according to the invention. According to a further embodiment of the invention, the neurological or inflammatory response is Parkinson's disease.

Methods for treating Parkinson's disease are disclosed according to the invention. According to an embodiment of the invention, the activity of protein kinase Cδ (PKCδ) is modulated by administering a rottlerin analog according to the invention. Treatment methods according to the invention inhibit the progression of neuronal cell death caused by Parkinson's disease.

A further embodiment of the invention includes a pharmaceutical composition for treating a neurological or inflammatory response mediated by protein kinase C (PKC) in an animal. Pharmaceutical compositions according to the invention may comprise, consist of or consist essentially of a rottlerin analog according to invention and a pharmaceutically acceptable carrier.

As used herein, "treating" or "treatment" of a state, disorder or condition includes: (1) preventing or delaying the appearance of clinical symptoms of the state, disorder or condition developing in a mammal (subject) that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statically significant or at least perceptible to the patient or to the physician.

As used herein, a "therapeutically effective amount" means the amount of a rottlerin analog or compound derived therefrom that, when administered to a mammal (subject) for treating a disease, disorder or condition, is sufficient to effect such treatment. The "therapeutically effective amount" will vary depending on particular rottlerin analog or compound derived therefrom, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is the highest safe dose according to sound medical judgment. The rottlerin analogs or compounds derived therefrom of the invention may be administered in therapeutically effective amounts, alone or in a cocktail with other compounds.

The rottlerin analogs or compounds derived therefrom of the invention may be administered to subjects (animals, most particularly mammals including humans) afflicted with any disease, disorder or condition characterized by neurological and/or inflammatory responses mediated by protein kinase C, particularly PKCδ. In particular, rottlerin analogs or compounds derived therefrom of the invention are believed useful in treating the neurological and/or inflammatory responses associated with Parkinson's disease, by administering to a subject with Parkinson's disease an effective amount of a rottlerin analog or compound derived therefrom according to invention.

The rottlerin analogs or compounds derived therefrom of the invention may also be useful in the treatment of Parkinson's disease and other related neurological conditions (e.g. Lewy body diseases, Alzheimer disease). Thus, a method for treating, inhibiting or delaying the onset of Parkinson's disease in a subject is provided comprising administering to a subject in need of such treatment an effective amount of a rottlerin analog or compound derived therefrom according to the present invention.

In order to facilitate administration, rottlerin analogs or compounds derived therefrom may be mixed with any of a variety of pharmaceutically acceptable carriers for administration. "Pharmaceutically acceptable" as used herein means that the rottlerin analogs or compounds derived therefrom or composition is suitable for administration to a subject to achieve the treatments described herein, without unduly deleterious side effects in light of the severity of the disease and necessity of the treatment. The carrier may be a solid or a liquid, or both, and is preferably formulated with the compound as a unit-dose formulation, for example, a tablet, which may contain from about 0.1% to 99% by weight of the active compound. Pharmaceutical compositions may be prepared by any of the well known techniques of pharmacy consisting essentially of mixing the components, optionally including one or more pharmaceutical additives.

Dose ranges can be adjusted as necessary for the treatment of individual patients and according to the specific condition treated. Any of a number of suitable pharmaceutical formulations may be utilized as a vehicle for the administration of the compositions of the present invention and maybe a variety of administration routes are available. The particular mode selected will depend of course, upon the particular formulation selected, the severity of the disease, disorder, or condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes and the like. Accordingly, the formulations of the invention include those suitable for oral, rectal, topical, buccal, parenteral (e.g., subcutaneous, intramuscular, intradermal, inhalational or intravenous) and transdermal administration, although the most suitable route in any given case will depend on the nature and severity of the condition being treated and on the nature of the particular active product used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately mixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by mixing the compound with water or a glycerin buffer and rendering the resulting solution sterile and isotonic with the blood. Alternately, the extracts, fractions thereof or compounds thereof can be added to a parenteral lipid solution.

Formulations suitable for rectal administration are preferably presented as unit dose suppositories. These may be prepared by mixing the active compound with one or more conventional solid carriers, for example, cocoa butter, and then shaping the resulting mixture.

Formulations of the inventive mixtures are particularly suitable for topical application to the skin and preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current to "inject" electrically charged ions into the skin) through the skin. For this, the dosage form typically takes the form of an optionally buffered aqueous solution of the active compound. Suitable formulations comprise citrate or bis/tris buffer (pH 6) or ethanol/water and contain from 0.01 to 0.2M active ingredient.

Mammals may be treated using the methods of the present invention and are typically human subjects although the methods of the present invention may be useful for veterinary purposes with a variety of other subjects.

Embodiments of the present invention are further defined in the following non-limiting Examples. It should be understood that these Examples, while indicating certain embodiments of the invention, are given by way of illustration only. From the above discussion and these Examples, one of ordinary skill in the art can ascertain the essential characteristics of this invention and, without departing from the spirit and scope thereof, can make various changes and modifications of the embodiments of the invention to adapt it to various usages and conditions. Thus, various modifications of the embodiments of the invention, in addition to those shown and described herein, will be apparent to those of ordinary skill in the art from the foregoing description. Such modifications are also intended to fall within the scope of the appended claims.

Example 1

Preliminary neuroprotective screening studies with a variety of PKCδ-related analogs were performed with the well characterized rat mesencephalic dopaminergic cells, known as N27 cells. Various analogs were tested and synthesized for testing in order to elucidate which segments of the rottlerin skeleton are crucial for activity. Results from this cell culture model are readily reproducible in primary cultures and animal models, and have been demonstrated to be a valid cell model These studies demonstrate the findings from the cell culture model to animal models of Parkinson's disease, showing the effectiveness of the PKCδ analogs of the present invention.

Studies with First Generation PK Analogs:

A first generation of rottlerin analogs was utilized for neuroprotection studies, as shown as PK101-103 in FIG. 1. A first generation of compounds (identified here as rottlerin analogs (PK101-103) are known compounds having some structural relation to rottlerin. These were tested in an N27 dopaminergic cell model for their neuroprotective properties. PK101-103 are known compounds and were not synthesized using the methods according to the present invention. The compounds were tested to determine the structural and functional relationships to rottlerin based on MMP+-induced caspase-3 activation, cytotoxic and apoptotic cell death.

The N27 cells were exposed to 300 μM MPP+ for 24 hr in the presence or absence of three different PKCδ compounds (PK101-103) in the dose range of 0.1-10 μM. At the end of the treatment, cytotoxicity was measured using the Sytox cell death assay in a 96-well fluorescence microplate reader. Analogs PK101-103 protected N27 cells from MPP+-induced cytotoxicity in a dose-dependent manner. FIG. 1 shows significant blockage of MPP+-induced cytotoxicity in N27 cells co-treated with 3 μM PK101, PK102, and PK103.

To determine whether PK analogs are neuroprotective against MPP+-induced increases in caspase-3 and DNA fragmentation, their effects on MPP+-induced increases in caspase-3 activity and DNA fragmentation, markers of apoptotic cell death, were examined. All three analogs PK101-103 protected N27 cells from MPP+-induced caspase-3 activation and DNA fragmentation. FIG. 1 shows significant blockage of MPP+-induced increases in caspase-3 activation and DNA fragmentation in N27 cells co-treated with 3 μM PK101, PK102, and PK103. Initial toxicological screenings showed these compounds are not toxic at up to 500 μM concentrations. ($p<0.01$ and *$p<0.001$, compared to vehicle control; #$p<0.05$, ##$p<0.01$, compared to MPP+ treatment).

Figure 2:
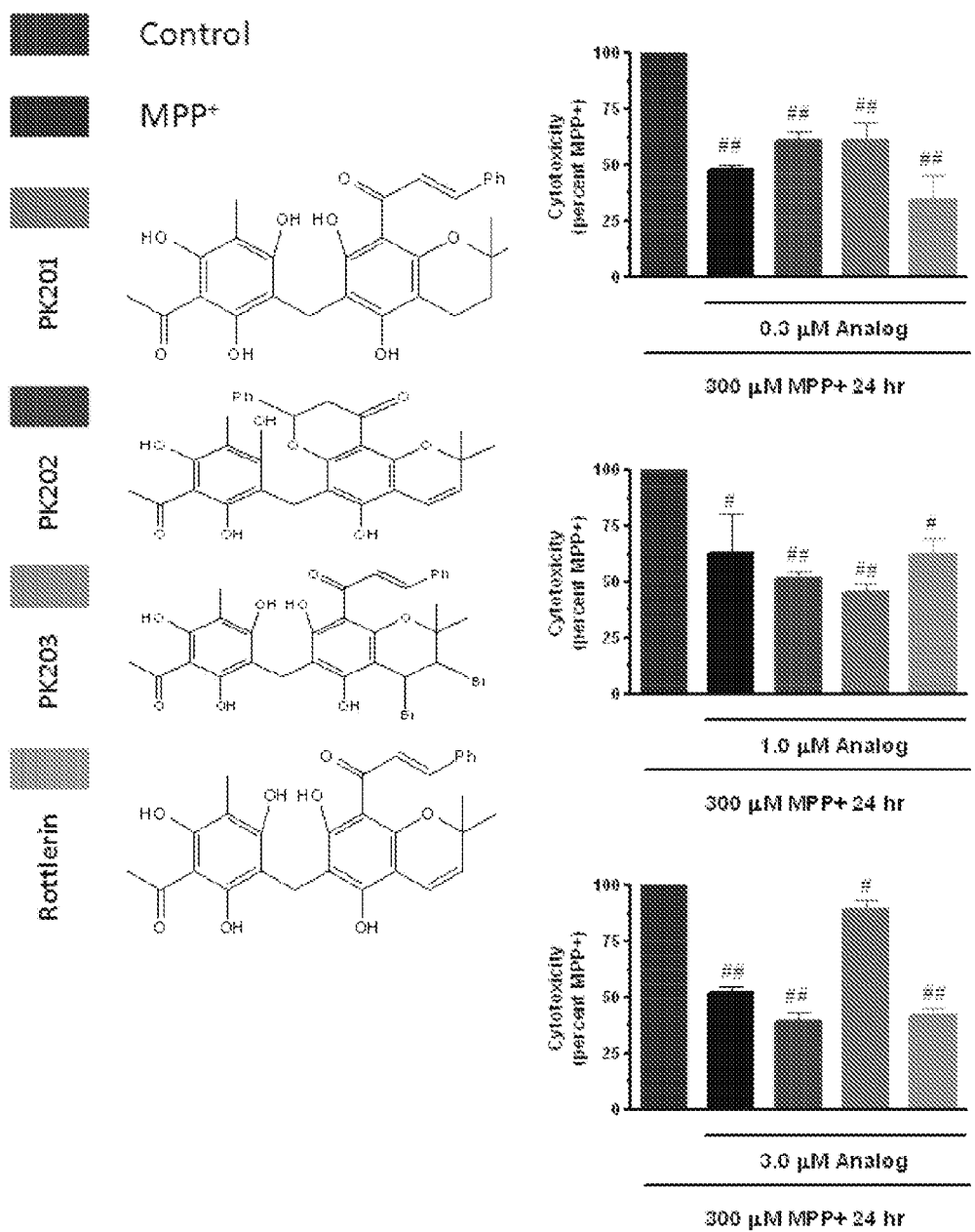
FIG. 2 illustrates the effect of second generation PK analogs on MPP+-induced cytotoxicity. The effect of blockage of MPP+-induced cytotoxicity in N27 cells co-treated with 0.3, 1 and 3 μM PK201, PK202, and PK203 is shown.

Studies with Second Generation PK Analogs:

A second generation of rottlerin analogs was further utilized for neuroprotection studies, as shown as PK201-203 in FIG. 2. The second generation of compounds (identified here as rottlerin analogs (PK201-203) were tested to compare the neuroprotective effect of PK analogs PK201-PK203 against MPP+-induced cytotoxic cell death. Based on the results obtained with first generation analogs, the three second generation rottlerin analogs (PK201-203) were tested. The compounds were tested in an N27 dopaminergic cell model for their neuroprotective properties. N27 cells were exposed to 300 μM MPP+ for 24 hr in the presence or absence of three different PK compounds (PK201-203) in the dose range of 0.3-3 μM.

At the end of the treatment, cytotoxicity was measured using the Sytox cell death assay in a 96-well fluorescence microplate reader. Analogs PK201-203 protected N27 cells from MPP+-induced cytotoxicity in a dose-dependent manner. FIG. 2 shows significant blockage of MPP+-induced cytotoxicity in N27 cells co-treated with 0.3, 1 and 3 μM PK201, PK202, and PK203. These results suggest that PKCδ inhibitor analogs PK201-203 effectively protected dopaminergic cells against MPP+-induced cytotoxic cell death; PK202 analog was the most potent inhibitor.

Figure 3:
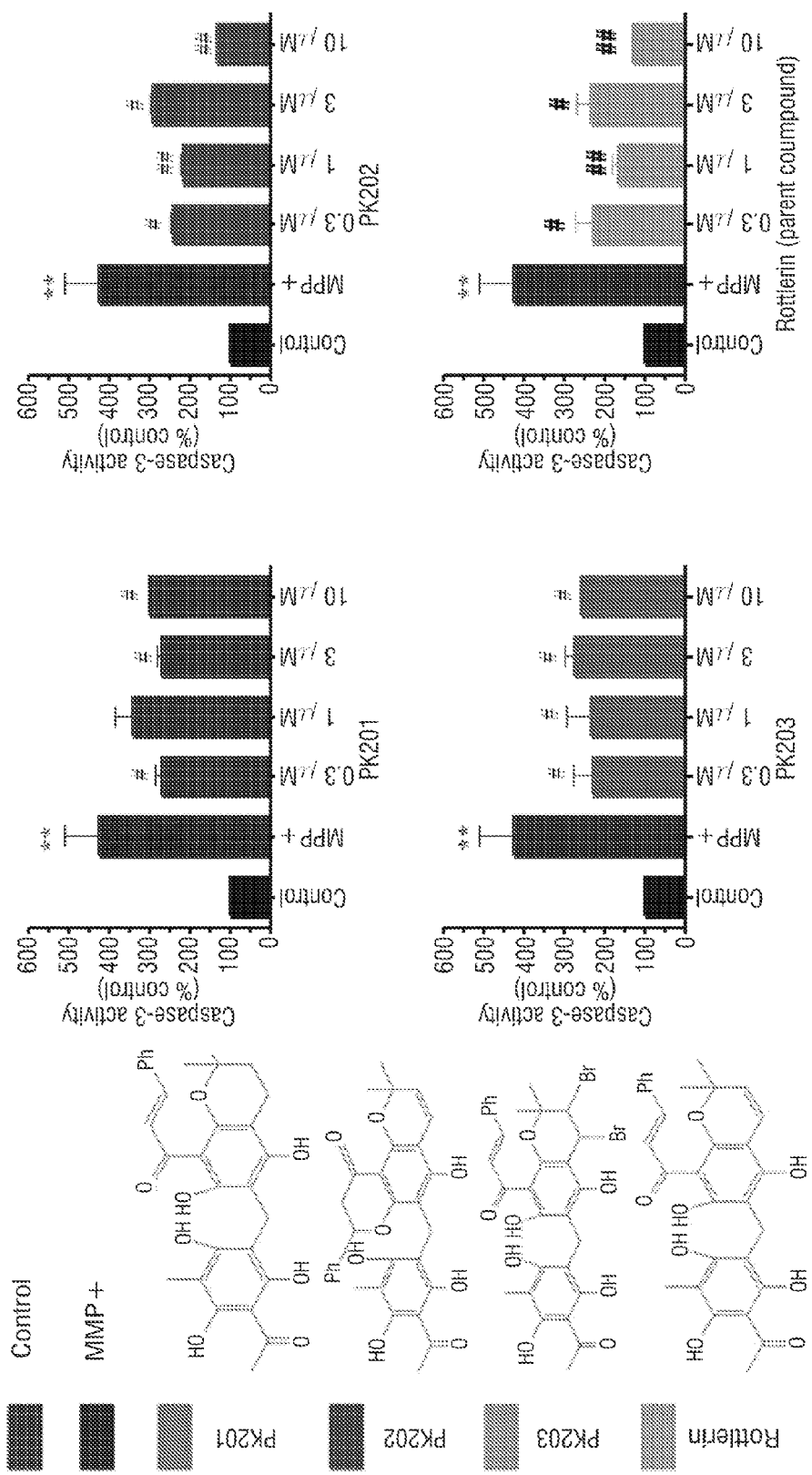
FIG. 3 illustrates the effect of second generation PK analogs on MPP+-induced caspase-3 activity. The effect of blockage of MPP+-induced caspase-3 activity in N27 cells co-treated with 0.3, 1, 3 and 10 μM PK201, PK202, and PK203 is shown.
Figure 4:
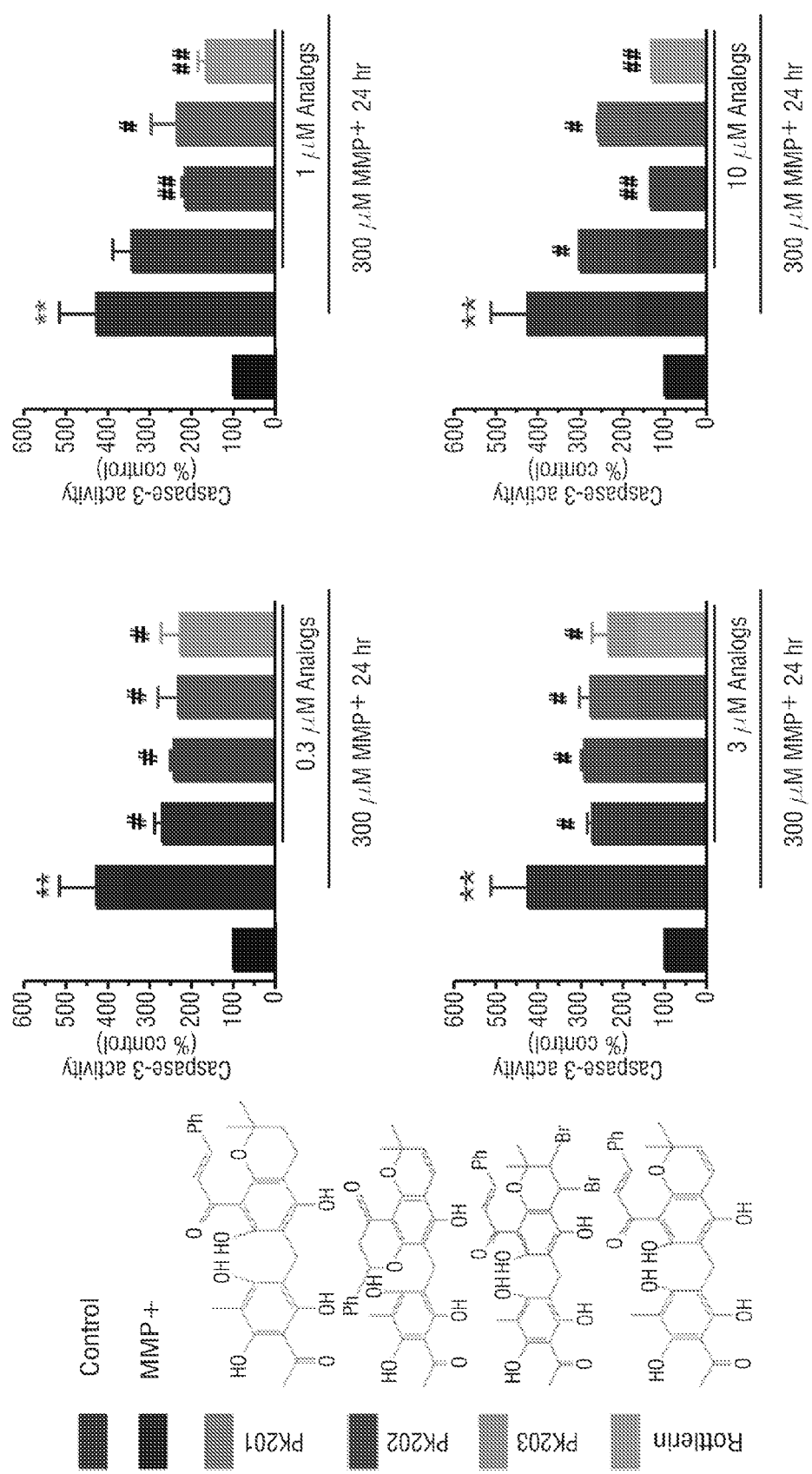
FIG. 4 illustrates the comparison of the second generation analogs PK201, PK202, and PK203 on MPP+-induced caspase-3 activation at various inhibitor concentrations.

The second generation PK analogs were further tested to determine whether the analogs are neuroprotective against MPP+-induced apoptotic cell death. The effects on MPP+-induced increases in caspase-3 enzymatic activity were analyzed, a marker of apoptotic cell death. N27 cells were exposed to 300 μM MPP+ for 24 hr in the presence or absence of three different PKC5 compounds (PK201-203) in the dose range of 0.3-10 μM. At the end of the treatment, cytotoxicity was measured using the caspase-3 assay in a 96-well fluorescence microplate reader. Analogs PK201-203 protected N27 cells from MPP+-induced cytotoxicity in a dose-dependent manner. FIG. 3 shows a dose-dependent blockage of MPP+-induced caspase-3 activity in N27 cells co-treated with 0.3, 1, 3 and 10 μM PK201, PK202, and PK203. Data showing the comparison of the analogs at each inhibitor concentration are shown in FIG. 4, suggesting that among the second generation PKCδ inhibitor analogs, PK202 more effectively protects dopaminergic cells against MPP+-induced caspase-3 activity, a marker of apoptotic cell death, than PK201 and PK203.

These results demonstrate the importance of particular structural groups on the function of the various PK201-203 analogs. PK201 and PK203 lack a double bond in the oxygen-containing ring of the compound, resulting in less biological activity. This double bond is present in the more-effective PK202 and rottlerin, suggesting the importance of the double bond in any rottlerin analog. Additionally, the halogen bromine was added to the compound PK203 on the oxygen-containing ring and also demonstrated decreased biological activity over PK202 and rottlerin. The study of PK201-203 provided additional direction for the desired structural characteristics of a synthesized rottlerin analog.

Example 2

Synthesis of an active rottlerin analog is shown below through a four-step sequence. In vitro testing demonstrates the importance of the hydroxyl groups and the alkene subunit. The four-step sequence of synthesis yields gram quantities of the rottlerin analog from commercially-available phloroglucinol (1,3,5-trihydroxybenzene). Organic phloroglucinol is polyfunctional and exists in two tautomers (1,3,5-trihydroxybenzene and 1,3,5-cyclohexanetrione) that remain in equilibrium.

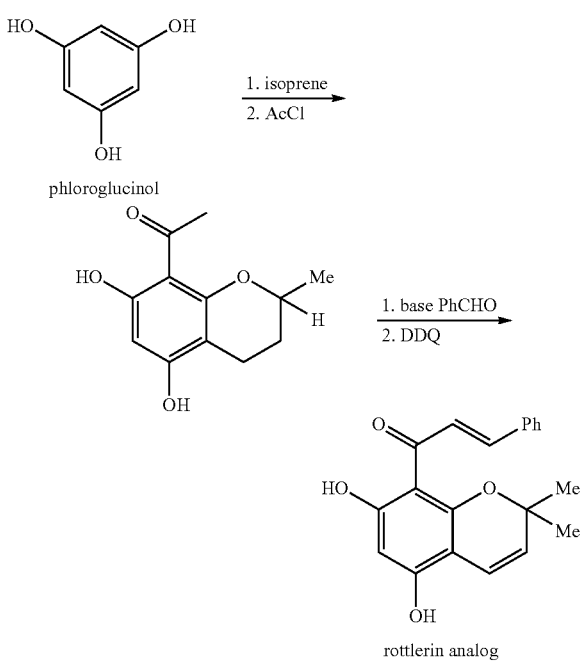

The synthesis of the base rottlerin analog from the commercially-available phloroglucinol provides a synthesis from an inexpensive commercial material. The first step is the addition of the oxygen-containing ring to the phloroglucinol. Dry phloroglucinol is dissolved in 1,4-dioxane. A catalyst (such as a solid acid catalyst as Amberlyst 15) is utilized for the reaction. The intermediate is purged with argon and cooled to 0° C. with stirring. Isoprene is added drop wise with a long condenser to minimize escape of the isoprene; then heated to reflux (90° C.) for 18 hours. The reaction is cooled and the catalyst is filtered off. The intermediate is washed, filtered, concentrated and purified to obtain a pure intermediate product (yielding approximately 54.3%).

The second step is to add the cinnamoyl group, through a Friedel-Crafts acylation followed by an aldol condensation with an aromatic aldehyde such as benzaldehyde. This process can be utilized to add any variety of aromatic aldehydes. Notably, this can be done in either a one or two-step process to generate the novel chemical structure illustrated as compound 4 (below in NMR analysis). However, the yield significantly improves with a two-step process. The steps include dissolving the intermediate in acetic acid (AcOH) and adding acetic anhydride and boron trifluoride etherate under argon with stirring; heat to 100° C. for three hours then cool to add sodium hydroxide to adjust the pH to between about 3 and 4. Then extract with ethyl acetate, wash, dry over MgSO4 and filter.

Chromatography shows two intermediates produced (below in NMR analysis). The intermediates are then dissolved in alcohol and KOH with the aromatic aldehyde under argon with stirring for 48 hours at room temperature. The intermediate is then extracted, washed, filtered and purified to obtain a pure intermediate product (yielding approximately 60%) of the intermediate with the carbonyl double bonded to the phenyl group.

Finally, adding the double bond to the oxygen-containing ring is the last addition to synthesis steps for generating a rottlerin analog structure. The reagent 2,3-dichloro-5,6-dicyanobenzoquinone (DDQ) and benzene are added to the intermediates under argon with stirring. They are heated overnight and then filtered and washed with sodium bicarbonate, then water. The product is then filtered, washed and concentrated to obtain the product analog (yielding approximately 80%).

Upon completion of the rottlerin analog shown above, additional synthesis steps may be employed to add additional functional groups to the analog. For example, numerous substitutions may be contemplated by one skilled in the art at the phenyl group and on the benzene ring between the two hydroxyl groups, while maintaining or exceeding the desired biological activity of rottlerin.

Persons of ordinary skill in the art will readily appreciate that the processes described above may in some instances be combined or separated into several steps. Further, persons of ordinary skill in the art will also readily appreciate that the processes of this invention may be accomplished using a variety of equipment and techniques that are well known in the art. The specific equipment and processes used are not crucial so long as the intended result is accomplished. It should be appreciated that minor modifications of the composition and the ranges expressed herein may be made and still come within the scope and spirit of the present invention.

Example 3

NMR analysis of various rottlerin analog intermediates according to the synthesis embodiments of the invention were completed.

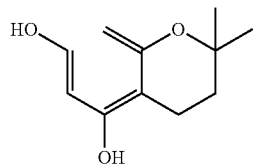

Compound 1. 1H NMR (400 MHz, (CD3)2CO) δ 5.95 (1H, d, J=2.0 Hz), 5.79 (1H, d, J=2.4 Hz), 2.54 (2H, t, J=13.6 Hz), 1.72 (2H, t, J=13.6 Hz), 1.25 (6H, s).

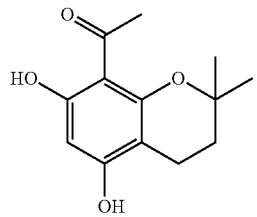 [SMILES: CC(=O)c1c(O)cc(O)c2c1OC(C)(C)CC2]

Compound 2. 1H NMR (400 MHz, (CD3)2CO) δ 5.94 (1H, s), 2.59 (2H, t, J=11.2 Hz), 2.57 (3H, s), 1.761 (2H, t, J=13.6 Hz), 1.37 (6H, s).

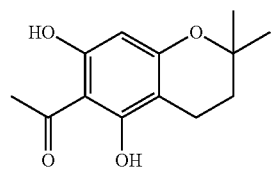 [SMILES: CC(=O)c1c(O)cc2c(c1O)CCC(C)(C)O2]

Compound 3. 1H NMR (400 MHz, (CD3)2CO) δ 5.86 (1H, s), 2.60 (3H, s), 2.52 (2H, t, J=12.8 Hz), 1.78 (2H, t, J=13.6 Hz), 1.30 (6H, s).

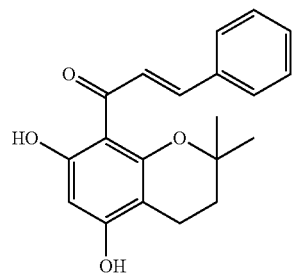 [SMILES: CC1(C)CCc2c(O)cc(O)c(C(=O)/C=C/c3ccccc3)c2O1]

Compound 4. 1H NMR (400 MHz, CDCl3) δ 8.05 (1H, d, J=8.2 Hz), 7.80 (1H, d, J=15.8 Hz), 7.61 (2H, d, J=7.6 Hz), 7.42 (3H, m), 5.91 (1H, s), 2.67 (2H, t, J=16.1 Hz), 1.89 (2H, t, J=11.7 Hz), 1.49 (6H, s).

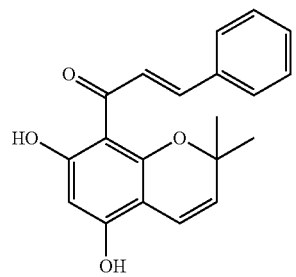 [SMILES: CC1(C)C=Cc2c(O)cc(O)c(C(=O)/C=C/c3ccccc3)c2O1]

Compound 5. 1H NMR (400 MHz, CDCl3) δ 8.05 (1H, d, J=8.2 Hz), 7.80 (1H, d, J=15.8 Hz), 7.61 (2H, d, J=7.6 Hz), 7.42 (3H, m), 6.67 (1H, d, J=14.2 Hz), 5.94 (1H, s), 5.60 (1H, d, J=8.8 Hz), 1.45 (6H, s).

Example 4

Studies with 3rd Generation PK Analogs.

Figure 5:
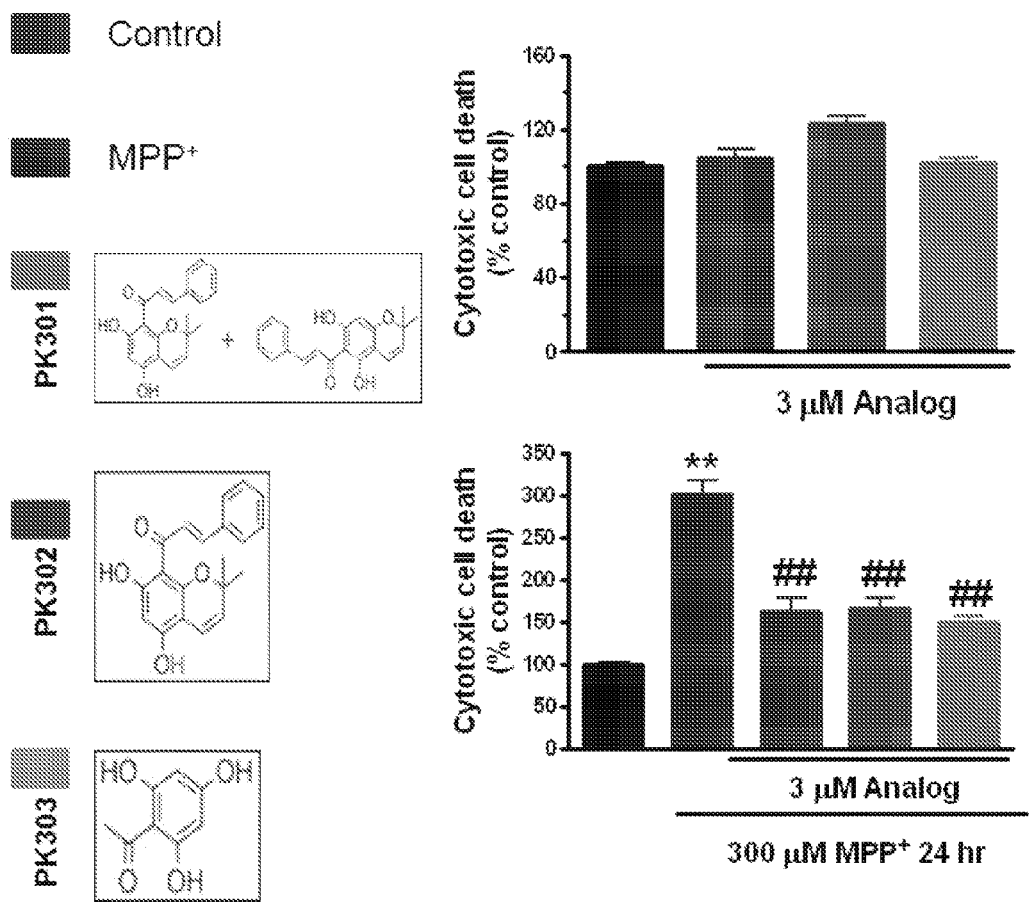
FIG. 5 illustrates the effect of third generation PK analogs on MPP+-induced cytotoxicity in N27 cells. The effect of blockage of MPP+-induced cytotoxicity in N27 cells co-treated with 0.3, 1 and 3 μM PK301, PK302 and PK303 is shown.

Based on the results of testing PK101-103 and PK201-203, a further comparison of the neuroprotective effect of PK analogs PK301-303 against MPP+-induced cytotoxic apoptotic cell death was examined. Third generation analogs were synthesized and named PK301-303 (as shown in FIG. 5). PK302 was synthesized according to the novel methods embodied by the invention. PK301 incorporates PK302 and an isomer for a comparison of the activity of PK302 from the isomer. PK303 is a potential starting material for the synthesis of rottlerin analogs according to the methods of the invention. PK303 is acytyl phloroglucinol.

The analogs were tested in an N27 dopaminergic cell model for their neuroprotective properties. N27 cells were exposed to 300 μM MPP+ for 24 hours in the presence or absence of three different PK compounds (PK301-303) in the dose range of 0.3-10 μM. At the end of the treatment, cytotoxicity was measured using the Sytox cell death assay in a 96-well fluorescence microplate reader. Analogs PK301-303 protected N27 cells from MPP+-induced cytotoxicity in a dose-dependent manner. FIG. 5 shows significant blockage of MPP+-induced cytotoxicity in N27 cells co-treated with 0.3, 1 and 3 μM PK301, PK302 and PK303, suggesting that the newly synthesized third generation analogs PK301-303 all effectively protect dopaminergic cells against MPP+-induced cytotoxic cell death. PK302 and PK303 analogs were more potent inhibitors than PK301.

Figure 6:
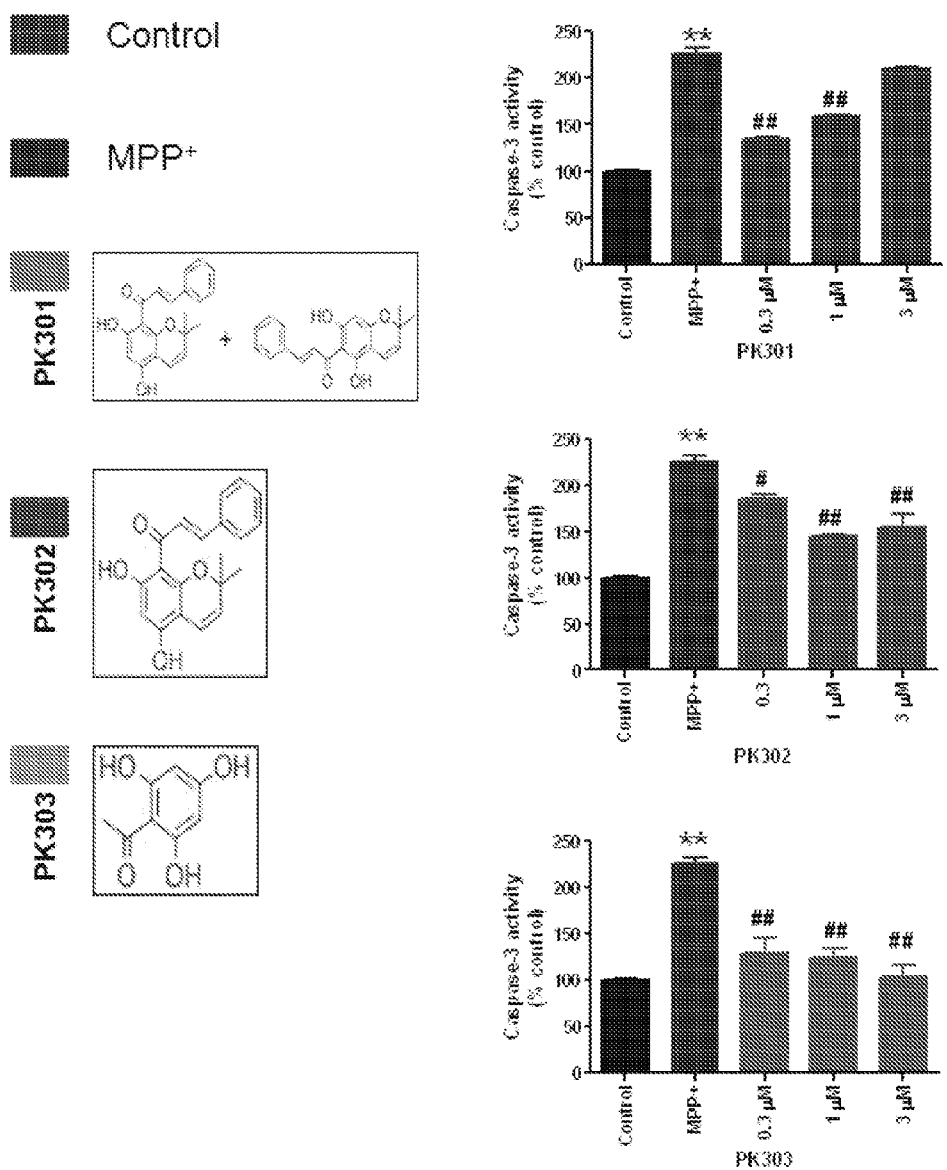
FIG. 6 illustrates the effect of third generation PK analogs on MPP+-induced caspase-3 activity. The effect of blockage of MPP+-induced caspase-3 activity in N27 cells co-treated with 0.3, 1, 3 and 10 μM PK301, PK302, and PK303 is shown.
Figure 7:
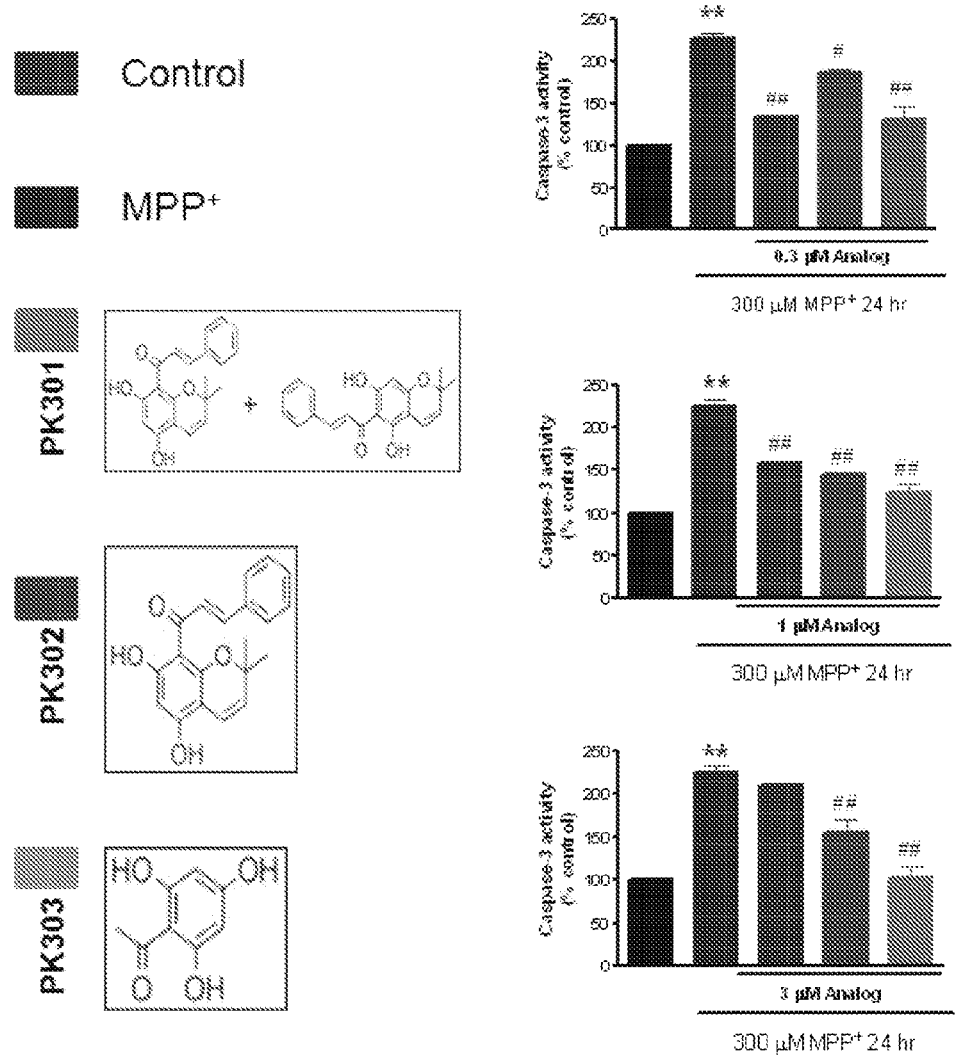
FIG. 7 illustrates the comparison of the third generation analogs PK301, PK302, and PK303 on MPP+-induced caspase-3 activation at various inhibitor concentrations.

The third generation PK analogs were further tested to determine whether the analogs are neuroprotective against MPP+-induced apoptotic cell death. The effects on MPP+-induced increases in caspase-3 enzymatic activity were examined, a marker of apoptotic cell death. N27 cells were exposed to 300 μM MPP+ for 24 hr in the presence or absence of three different PK compounds in the dose range of 0.3-10 μM. At the end of the treatment, cytotoxicity was measured using the caspase-3 assay in a 96-well fluorescence microplate reader. Analogs PK301-303 protected N27 cells from MPP+-induced cytotoxicity in a dose-dependent manner. FIG. 6 shows significant blockage of MPP+-induced caspase-3 activity in N27 cells co-treated with 0.3, 1, 3 and 10 μM PK301, PK302, and PK303. Data showing the comparison of the analogs at each inhibitor concentration are shown in FIG. 7. The results show that that among the newly synthesized PKCδ inhibitor analogs, PK302 and 303 more effectively protect dopaminergic cells against MPP+-induced caspase-3 activity, a marker of apoptotic cell death, than PK301.

Rat mesencephalic dopaminergic clonal cells (N27) were used and maintained in RPMI 1640 complete medium supplemented with 10% Fetal Bovine Serum, 1% L-glutamate and 1% Penicillin/Streptomycin in a 37° C. incubator with 5% CO2. After 4-6 days in culture, the cells were used for the experiments.

Example 5

A dose-dependent study of the effect of lead PK analogs on PKCδ enzyme activity in in vitro kinase assays was performed. After successful screening in cell culture studies, we selected the most efficacious PK analog from each of the three generations of PK analogs. These included PK103, PK202 and PK302, also referred to as lead PK analogs. The lead PK analogs were selected for further evaluation in preclinical animal studies.

Since PK analogs are directed against PKCδ, it was first determined whether the analogs would inhibit PKCδ enzyme activity in kinase assays. The ability of lead PK analogs to inhibit purified human recombinant PKCδ enzyme activity by 32P phosphorylation kinase assay with histone as the substrate was measured. The in vitro kinase assays were performed with human recombinant PKCδ in the presence or absence of 0.3-10 μM lead PK analogs in the presence histone substrate, [$^{32}$P]-ATP and phospholipids. The extent of histone phosphorylation was determined after separation in SDS-PAGE and by phosphoimaging. IC$_{50}$ was obtained using sigmoidal dose-response curve and non-linear regressional analysis using Graphpad Prism software.

Figure 8:
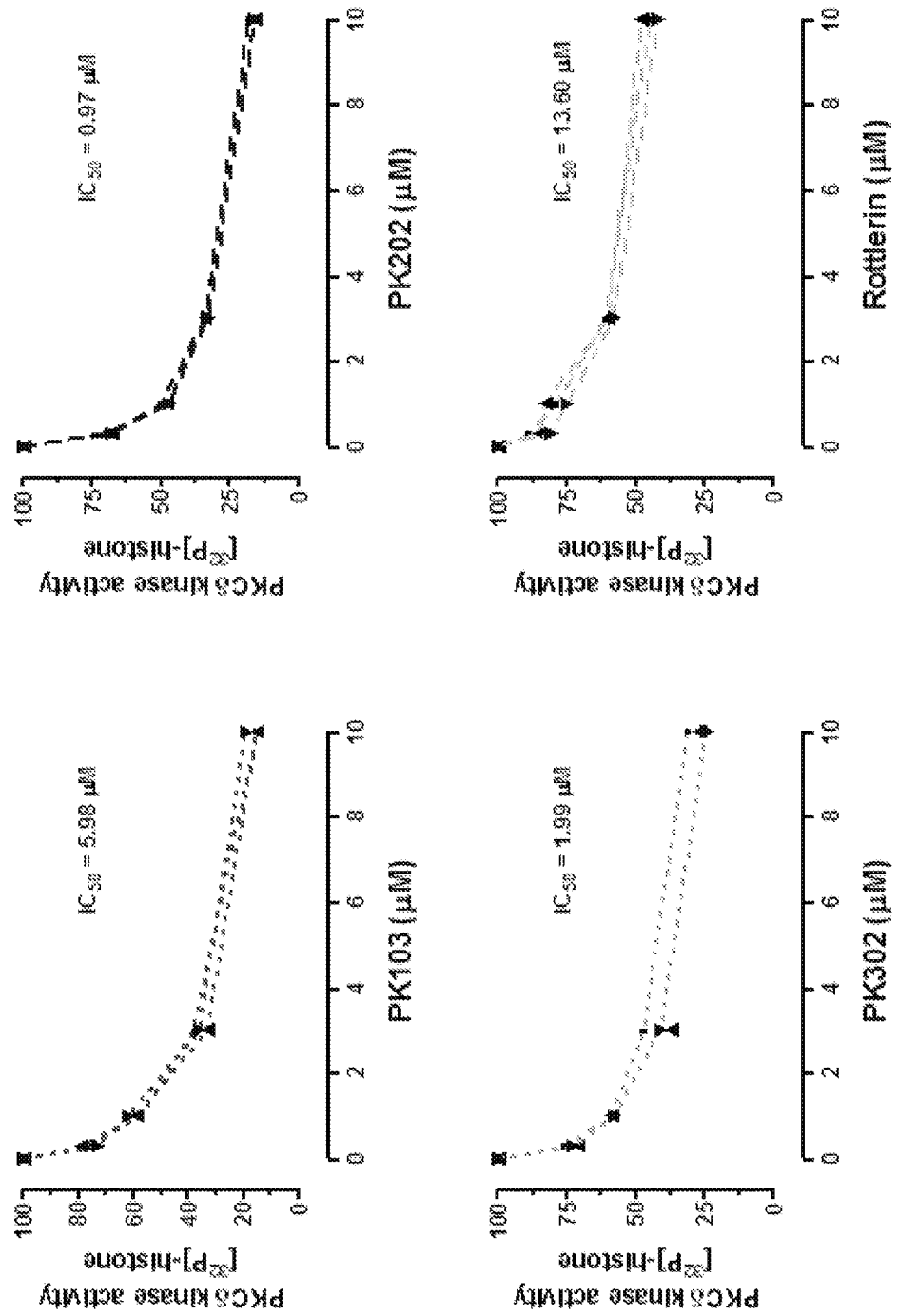
FIG. 8 illustrates the inhibitory effect of lead PK analogs on PKCδ kinase activity in vitro.

As shown in FIG. 8, parent compound and PK analogs PK103, PK202 and PK302 inhibited the therapeutic target PKCδ kinase activity in a dose-dependent manner with an IC50 of 5.98 μM for PK103, 0.97 μM for PK202, 1.99 μM for PK302 and 13.6 μM rottlerin. The lead PK analogs inhibited PKCδ kinase activity with an IC50 3-13-fold better than the parent compound rottlerin.

Example 6

Kinase profiling of PK analogs. The inhibitory effect of lead PK analogs were tested against a panel of 15 protein kinase targets (TABLE 1) to develop better lead candidates without "off" target effects. The selectivity assay was performed at Signal Chem™ (Richmond, BC, Canada) by profiling against protein kinase targets using the "Gold Standard" radioisotope screening assay format. This assay format gave the highest signal noise ratio and allowed the direct measurement of catalytic activity of a protein kinase.

All assays were performed in triplicate in a 96-well assay format and the % error between triplicates is <10%. Protein kinase assays was performed in the presence of 50 μM ATP at 30° C. for 15 min. The activity of the enzymes in the presence of 5 μM PK analogs was compared to that in the vehicle control and expressed as a percent change in activity relative to that observed in the vehicle control. In TABLE 1, the results are expressed as percent activity change compared to control. The intra-assay variability was determined to be less than 10%. Inhibition of target activity by the compound is shown by a negative value, while activation of target activity is shown by positive value, with values >10% considered to be highly significant.

TABLE 1

| Human Kinases | PK103 | PK202 | PK302 | Rottlerin |
|---|---|---|---|---|
| In-Vitro Kinase Profiling of Lead PK Compounds (5 μM, % activity change) | | | | |
| AKT1 | −6 | −12 | −10 | −14 |
| ASK1 | 0 | 4 | 0 | 2 |
| ERKI | 0 | 4 | 3 | 3 |
| CamK2a | 6 | 6 | 5 | 7 |
| JNK3 | −12 | −12 | −10 | 7 |
| P38α | −5 | −1 | −4 | −1 |
| PKAα | 3 | 10 | 1 | 1 |
| PKCα | −1 | 9 | 13 | −7 |
| PKCμ | 6 | 6 | 2 | −5 |
| PKCβ | 3 | 1 | 6 | 0 |
| PKCγ | 9 | 1 | 32 | 6 |
| PKCε | 5 | −3 | 6 | −25 |
| PKCη | 7 | 15 | 19 | 12 |
| P13K (p110b/p85a) | −6 | −2 | −8 | −10 |
| Protein Kinase Cδ (PKCδ) - Therapeutic Target | | | | |
| % activity change 3 μM | −65 | −67 | −73 | −40 |
| IC50, μM | 5.98 | 0.97 | 1.99 | 13.6 |

The profiling data for the compound PK103 against various protein kinase targets showed only weak inhibition of the JNK3 target. The JNK3 was inhibited by 12% compared to control at 5 µM concentration of PK103. The rest of the protein kinase targets showed no significant effects.

The profiling data for the compound PK202 against various protein kinase targets showed weak inhibition of the AKT1 and JNK3 targets. The AKT1 and JNK3 targets were both inhibited by 12%, compared to the control, at 5 µM concentration of PK202. In addition, the PKCη target showed weak activation of 15% compared to the control. The rest of the protein kinase targets showed no significant effects.

The profiling data for the compound PK302 against various protein kinase targets showed weak to moderate activation of the PKCγ and PKCη targets. The PKCγ and PKCη targets were activated by 32% and 19%, respectively, compared to control at 5 µM concentration of PK302. The rest of the protein kinase targets showed no significant effects.

The profiling data for the parent compound rottlerin against various protein kinase targets showed weak to moderate inhibition of the AKT1 and PKCε targets. The AKT1 and PKCε targets were inhibited by 14% and 25%, respectively, compared to control at 5 µM concentration of rottlerin. In addition, the PKCη target showed weak activation of 12% compared to control. The rest of the protein kinase targets showed no significant effects. One of compound (PK103) showed weak inhibition of JNK3 while the other 3 compounds showed both inhibition and activation of a few targets. AKT1 and JNK3 consistently showed inhibition by 2 out of the 4 compounds while the PKCη target consistently showed activation by 3 out of the 4 compounds. PKCγ showed activation by only compound PK302, while the target PKCε showed only inhibition by parent compound rottlerin.

These results demonstrate that all three lead PK analogs were effective in inhibiting human therapeutic target PKCδ. Despite the efficacy of inhibition for PKCδ, none of the analogs displayed any potent activity in the panel of 15 protein kinase targets, demonstrating the PK analogs have a favorable selectivity for the human therapeutic target PKCδ and lack any significant "off" target effects.

Example 7

Lead PK analogs protect against MPP$^+$-induced loss of TH+ neurons in primary mesencephalic cultures. To determine if lead PK analogs protect against degeneration of nigral dopaminergic neurons resulting from MPP+ neurotoxicity, mouse primary mesencephalic neuronal cultures (prepared from E16-18-day-old mice embryos) were exposed to 10 µM MPP$^+$ in the presence or absence of 3 µM of lead PK analogs, PK103, PK202, PK302 and parent compound rottlerin for 48 h, and then assessed the viability of dopaminergic neurons using the $^3$H-dopamine uptake assay. (***$p<0.005$ (vehicle versus MPTP. ##$p<0.01$ (PK analogs versus MPTP)). Mazindol, a dopamine reuptake inhibitor, was used as a positive control for the assay.

Figure 9:
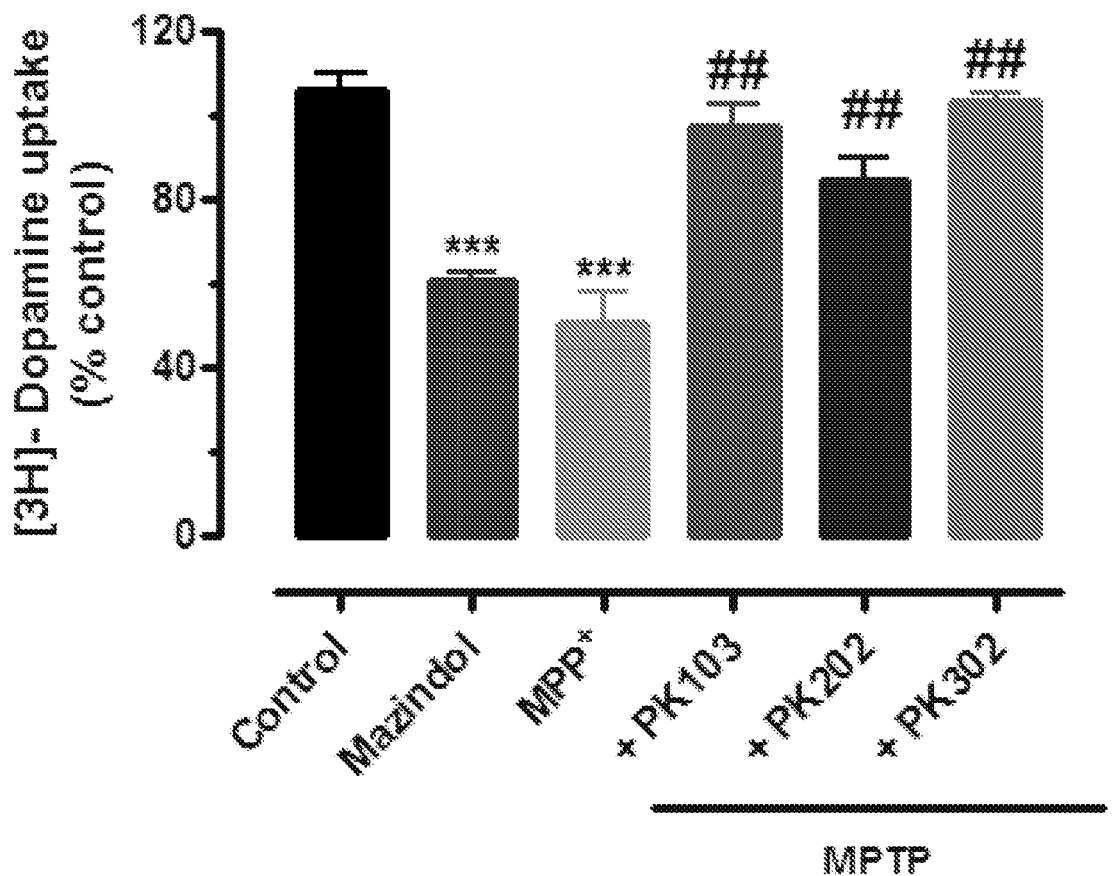
FIG. 9 illustrates lead PK analogs protect against MPP+-induced loss of dopamine uptake in mouse primary mesencephalic neurons.

FIG. 9 shows that treatment with MPP+ alone induced a significant decrease in dopamine uptake, indicative of a loss of nigral dopaminergic neurons, whereas all lead analogs, including rottlerin, protected against MPP$^+$-induced loss of dopaminergic neurons. The data confirm our findings obtained in the N27 dopaminergic cell model and demonstrate that the lead analogs are effective against dopaminergic neuronal degeneration in primary neuronal culture models.

Example 8

Lead PK analogs protect against behavioral deficits and neurochemical loss in a preclinical MPTP-induced mouse model of PD. After characterizing the neuroprotective effect of PK analogs in cell culture models of PD, as a proof of principle, preliminary evaluation of two lead PK analogs in an acute MPTP animal model of PD were conducted. C57 black mice received 4 doses of MPTP at 18 mg/kg i.p at 2 hr interval. Oral administration of lead PK analogs (10 mg/kg body wt, oral gavage) was started 1 day before MPTP insult and continued for 7 days. 1% DMSO was used as the vehicle control. Locomotor activity was measured using the Versa-Max Analyzer 1-2 days before sacrificing the mice. Mice were sacrificed after 7 days of MPTP injection. (n=5). (**$p<0.01$: PK analogs versus MPTP).

Figure 10B:
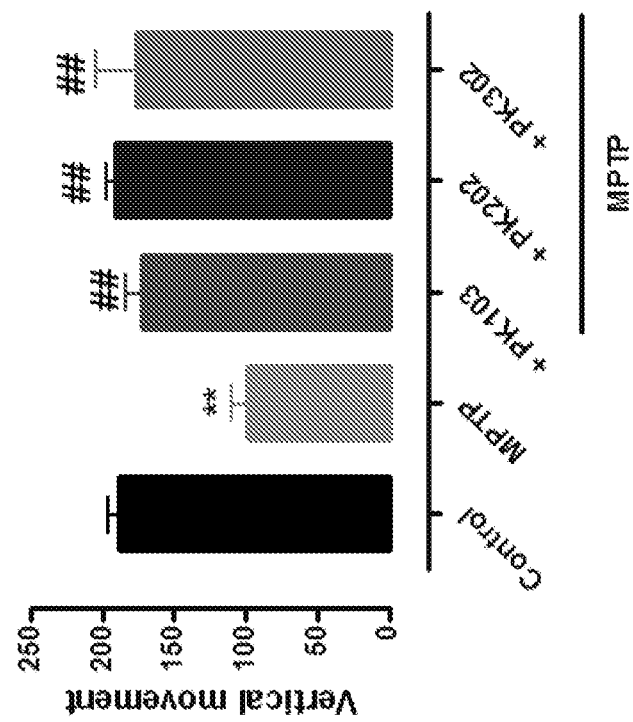
FIGS. 10A-B illustrate lead PK analogs protect against MPTP-induced motor deficits.
Figure 10A:
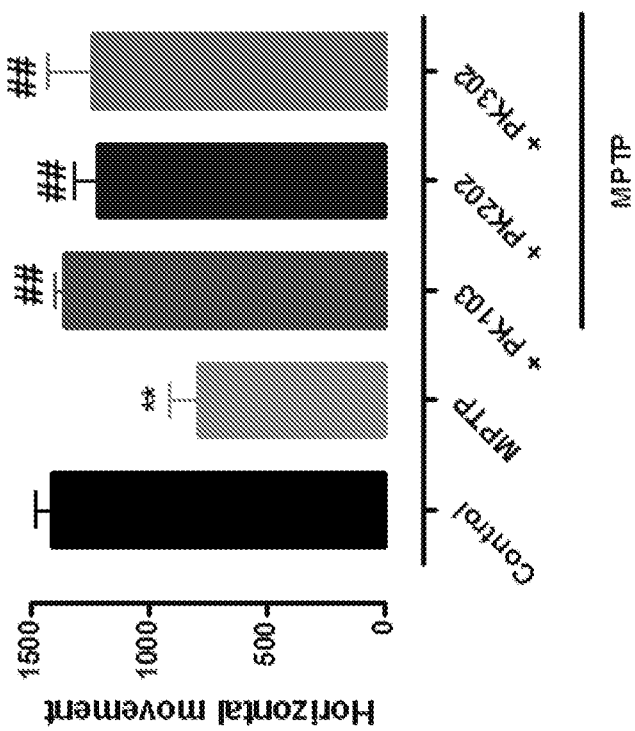
Figure 11B:
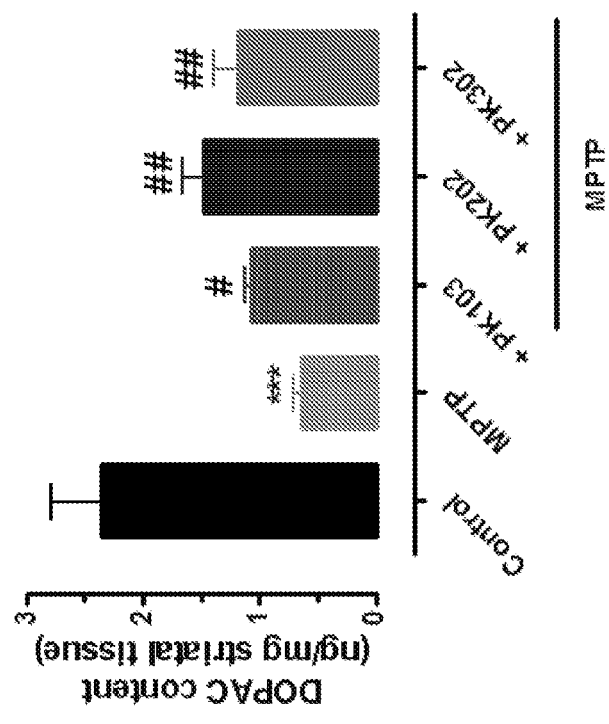
FIGS. 11A-B illustrate lead PK analogs protect against striatal DA and DOPAC depletion in acute MPTP-treated subjects.
Figure 11A:
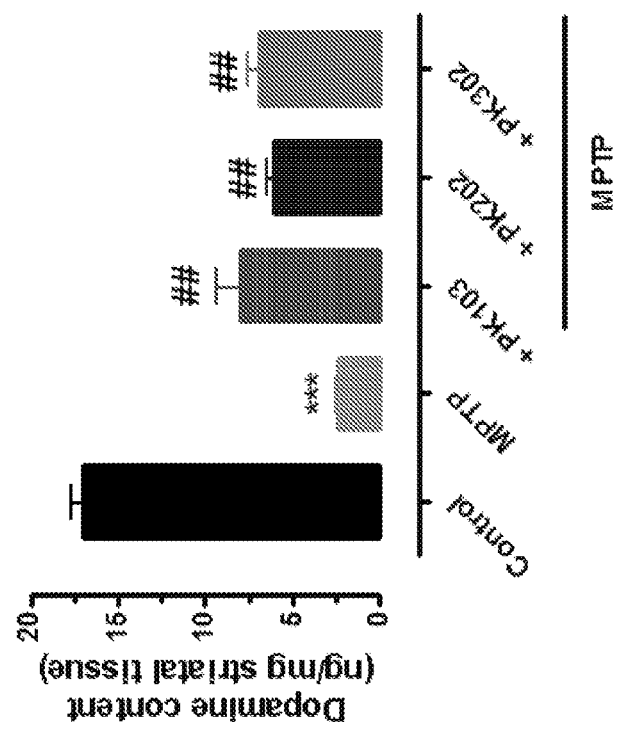

Preliminary investigation revealed that co-treatment with lead PK analogs, PK103, PK202 and PK302, significantly improved horizontal locomotor deficits (FIG. 10A), vertical locomotor deficits (FIG. 10B), attenuated striatal dopamine (FIG. 11A) and DOPAC depletions (FIG. 11B). The results demonstrate that lead PK analogs show significant efficacy for protecting against behavioral and neurochemical impairment in a well known preclinical model of PD.

Example 9

PK analogs attenuate dopaminergic neuronal cell loss induced by MPTP toxicity in mouse substantia nigra. Lead PK analogs were examined to determine whether they could protect against MPTP-induced dopaminergic neuronal loss in C57 black mice. Mice received 4 doses of MPTP at 18 mg/kg i.p. at 2 hr interval. Oral administration of PK analogs (10 mg/kg body wt, oral gavage) was continued for 7 days. Mice were sacrificed after 7 days of MPTP injections. (n=5).

Figure 12:
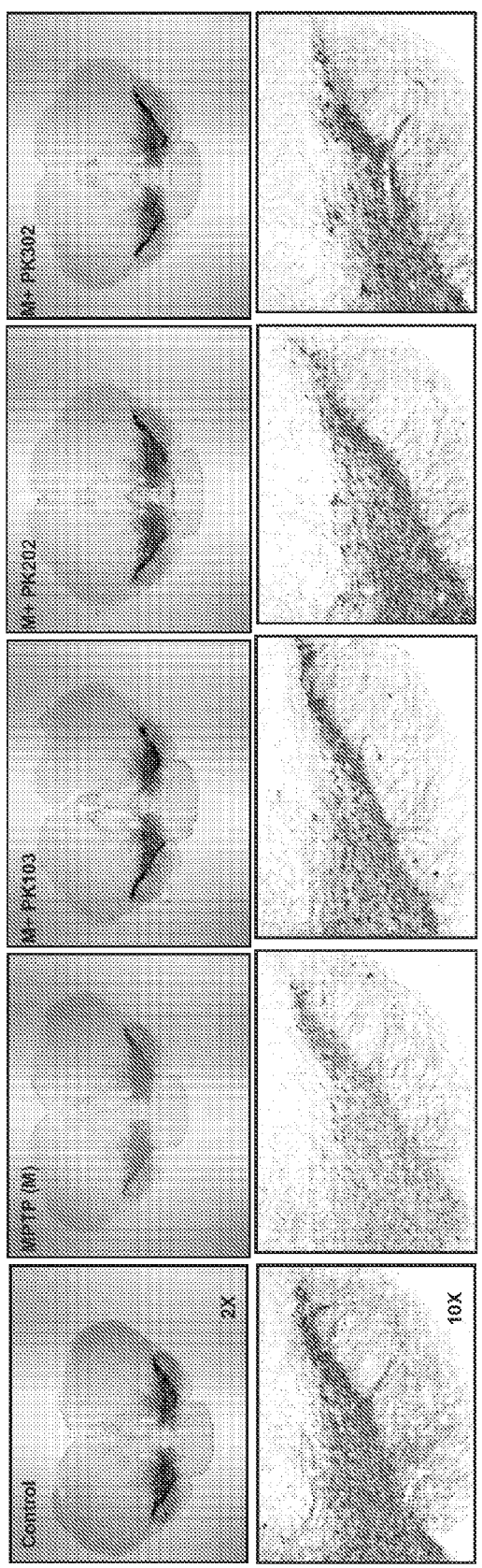
FIG. 12 illustrates that lead PK analogs rescue TH cell loss in MPTP-treated mouse substantia nigra.

The co-treatment with PK analogs PK103, PK202 and PK302 provided a significant protection against MPTP-induced nigral dopaminergic degeneration, as determined by tyrosine hydroxylase (TH) immunostaining (FIG. 12). As shown in FIG. 12, the substantia nigra was subjected to TH+ immunostaining by DAB. Abbreviataions: M: MPTP; SNpc: substantia nigra pars compacta; SNl: substantia nigra lateralis; SNr: substantia nigra reticularis; VTA: Ventral tegmental area.

These results show further evidence of significant efficacy of lead PK analogs in protecting against TH cell loss in a well-known preclinical model of PD.

Example 10

Bioavailability of Lead PK analogs. LC-MS-MS detection of lead PK analogs PK202 and PK8302 analog in mouse brain was completed. Significant levels of rottlerin in mouse brain substantia nigra after oral administration using LC-MS-MS was shown, demonstrating that rottlerin related compounds can effectively cross the blood brain barrier. Significant amounts of PK202 and PK302 analogs were detected in the substantia nigra of animals administered by oral gavage by LC-MS-MS, suggesting the analogs effectively crossed the blood brain barrier and exerted its neuroprotective effects.

Example 11

Neuroprotective effects of lead PK analogs against MPP$^+$-induced cytotoxic cell and apoptotic cell death. To address the ability to administer lead PK analogs as pharmaceutical compositions, we synthesized two analogs, PK111 analog in which both phenols were protected by methoxy group to reduce possible reactivity of phenol-OH functionality and PK112 analog in which conjugated side chain attached to one phenol to reduce degrees of freedom of the molecule and reduce possible rotational states. These two analogs were tested for ability to protect against MPP+-induced neurotoxicity and caspase-3 activation, a marker of apoptotic cell death, in N27 dopaminergic neuronal cell model.

Figure 14:
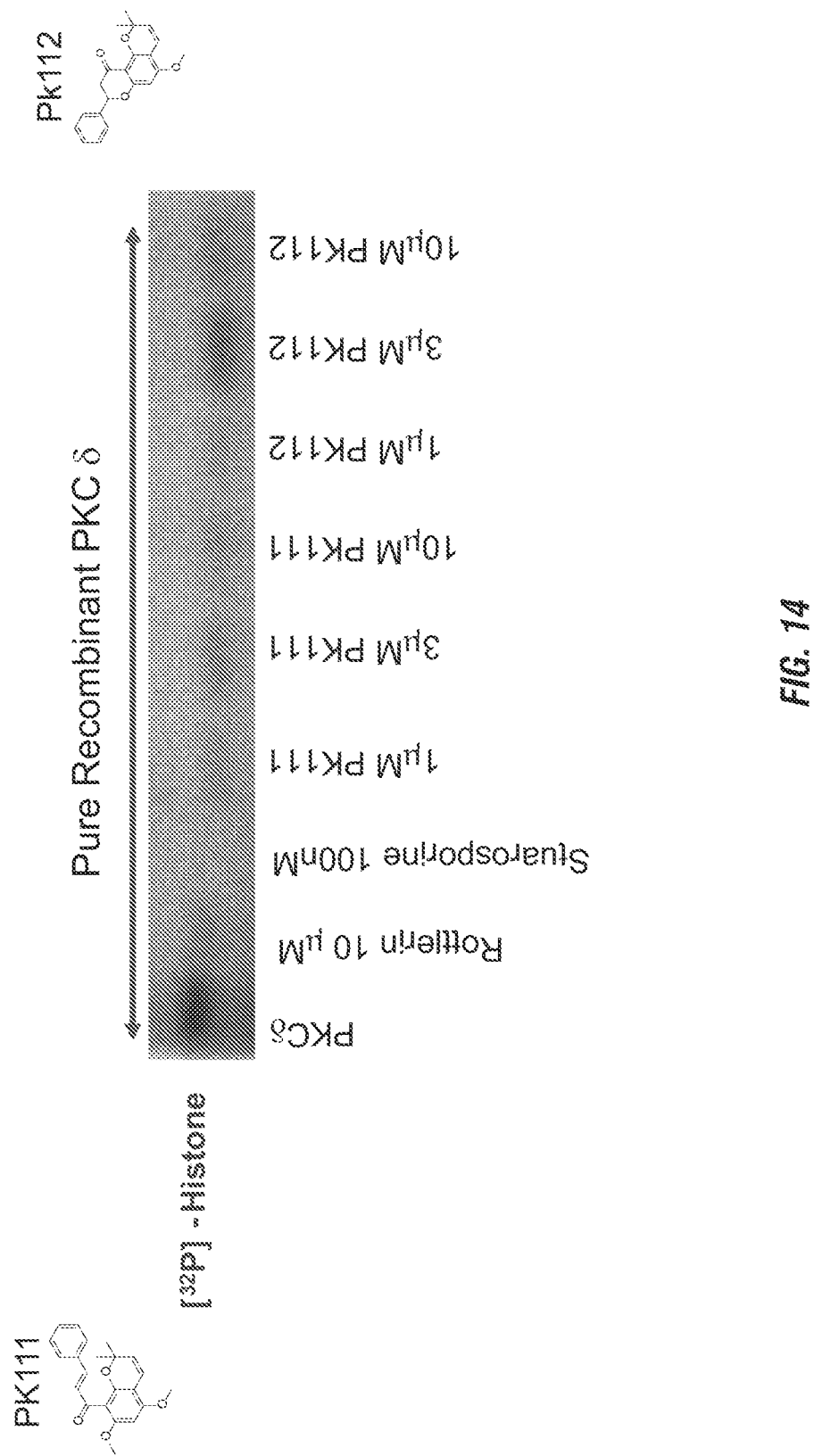
FIG. 14 illustrates the inhibitory effect of lead PK analogs on PKCδ kinase activity in vitro.

N27 cells were exposed to MPP+ for 24 hr in the presence or absence of PK analogs in the dose range of 1-30 µM. Both analogs PK111 and PK112 almost completely inhibited MPP+-induced caspase-3 activity (FIG. 13A) and cytotoxic cell death (FIG. 13B) and in dose-dependent manner and significantly exhibited better neuroprotection than the parent compound rottlerin. At higher doses (30 µM) analogs were toxic. Further, PK analogs PK111 and PK112 inhibited our therapeutic target PKCδ kinase activity in a dose-dependent manner in in vitro kinase assays using pure recombinant PKCδ protein (FIG. 14).

In vitro kinase assays were performed with human recombinant PKCδ in the presence or absence of 0.3-10 µM lead PK analogs in the presence histone substrate, [$^{32}$P]-ATP and phospholipids. The extent of histone phosphorylation was determined after separation in SDS-PAGE and by phospho-imaging.

Example 12

Design and Synthesis of Novel Rottlerin Analogs. Since Rottlerin has proven to be a difficult target to make synthetically, analogs have been developed and tested in an attempt to localize the region of activity and improve that activity. Initially, simple analogs of Rottlerin itself, obtained from Cal-BioChem (La Jolla, Calif., Cat #557370), were prepared and analyzed. Two compounds gave important results, one representing a simplified methylene linkage present in the parent compound (PK103), and the other (PK203) came from a simple bromination of natural Rottlerin. Both analogs showed less activity than Rottlerin, resulting in the hypothesis that the double bond present in the benzopyran ring of Rottlerin could be important to its activity.

Figure 15:
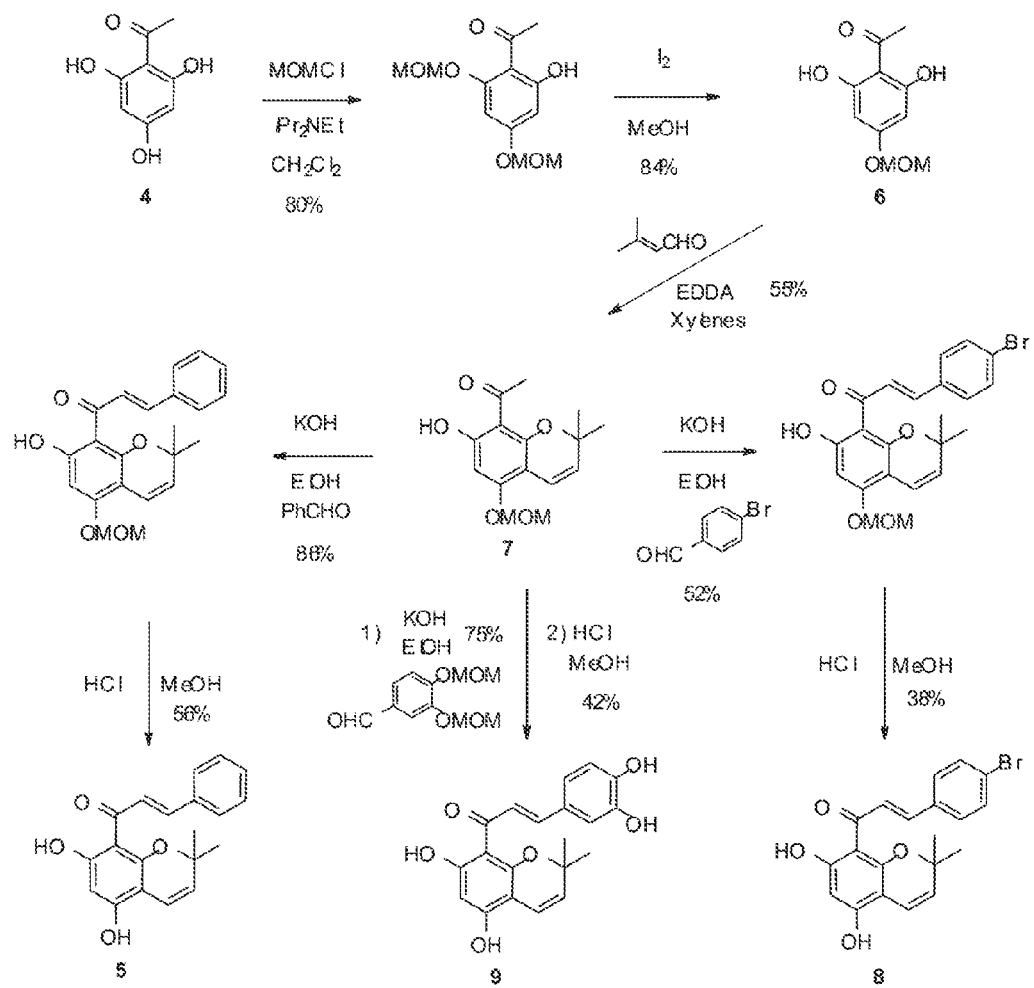
FIG. 15 illustrates synthesis of second and third generation PK analogs.

A second generation of analogs was developed pursuant to the identification of the importance of the double bond present in the benzopyran ring of Rottlerin (FIG. 15). These compounds were based on representing the left and right parts of Rottlerin, with the methylene linkage denoting the division.

The left part (4) was represented by commercially available 2',4',6'-trihydroxyacetopheone, while the right part (5) was synthesized, also starting with the acetophenone (4). Bis-MOM (methoxymethyl) protection of (4) was accomplished using MOMCl and selective deprotection occurred using iodine as the Lewis acid to give (6). Cyclization using ethylenediamine diacetate and 3-methyl-2-butenal in refluxing xylenes gave protected intermediate (7), which could be elaborated to the right part molecule (5) through an aldol condensation with benzaldehyde and then deprotection. Evaluation of these analogs confirmed the activity of Rottlerin lies in the right portion of the molecule.

Two new analogs (8, 9) were prepared, adjusting the electron density of the chalcone moiety by introducing a weak electron-donating group, bromine into the para position (8), and adding the catechol moiety (9) in the 3, 4-position to increase electron density. These analogs were synthesized in a similar manner as before, starting from intermediate (7), the aldol condensation was achieved using a substituted benzaldehyde to install the wanted group(s) on the chalcone system. In the case of analog (9), bis-protected aldehyde was used and all three protecting groups were removed at the same time in the final step.

Figure 16:
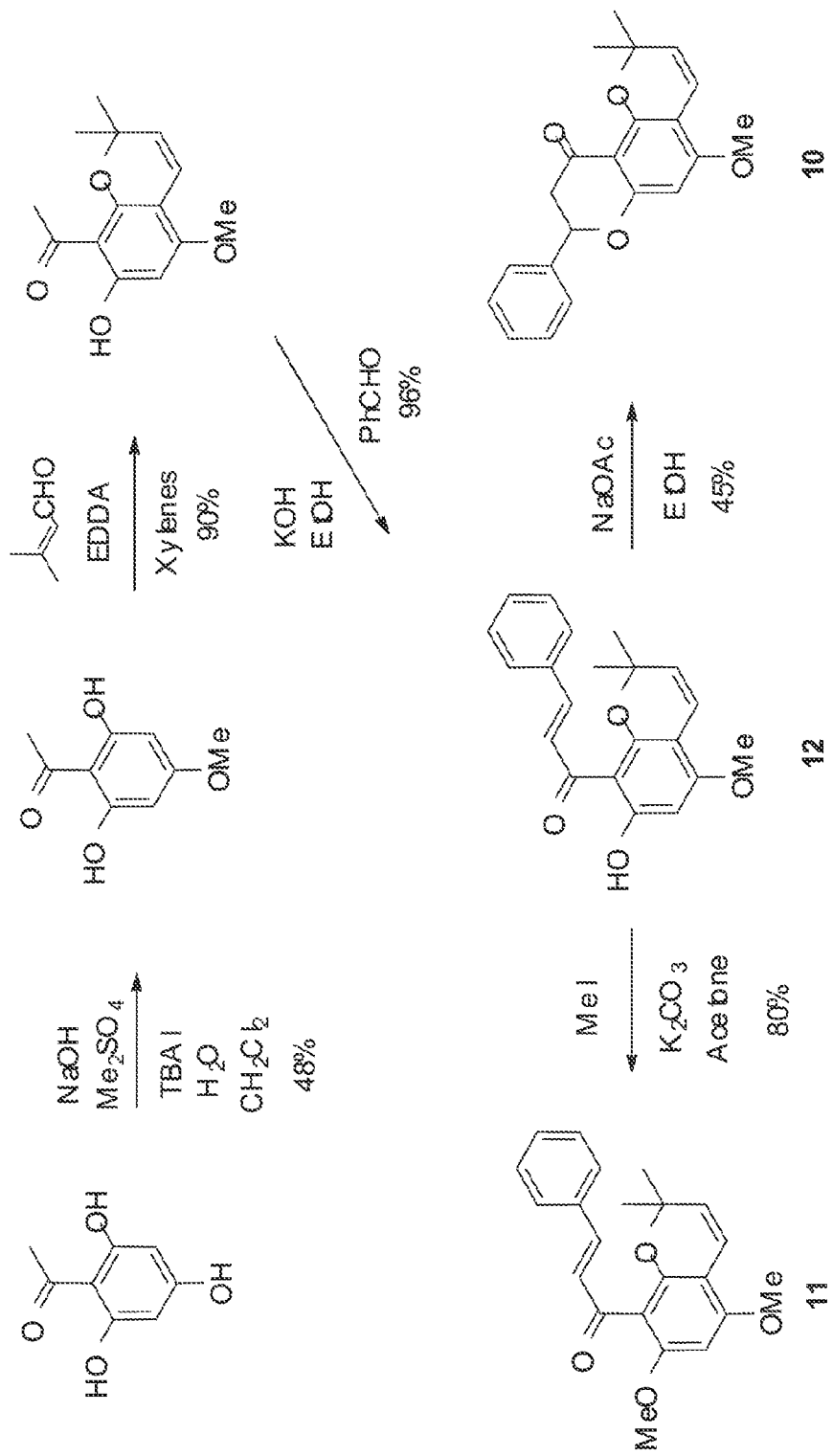
FIG. 16 illustrates synthesis of fourth generation PK analogs.

Limiting the rotational degrees of freedom of the molecule can also help increase activity. If the active site of the molecule is free to adjust its 3-dimensional geometry, there is less chance it will be in the needed position to interact with the receptor site. We decided to lock the rotation of the chalcone group by containing it in a 6-membered ring through a Michael addition process of the free aromatic hydroxyl group onto the enone double bond (10, FIG. 16). Our previous analogs featured free phenols. Due to their possible reactivity, this can be an issue for the drug when in the environment of the receptor site. This also tested the difference of the analogs when the phenols are protected as methoxy groups, or methyl ethers.

Another analog was made of our basic right part molecule 5 protected with methyl ethers (11). Both analogs were made using a slight modification to the synthesis, namely using a methyl ether (OMe) instead of a methoxymethyl (OMOM) ether. The key intermediate (12) could be methylated using methyl iodide to give analog (11), or cyclized using sodium acetate as base to give analog (10).

All publications and patent applications in this specification are indicative of the level of ordinary skill in the art to which this invention pertains. All publications and patent applications are herein incorporated by reference to the same extent as if each individual publication or patent application was specifically and individually indicated by reference. Therefore, the disclosure of each reference set forth herein is incorporated herein by reference in its entirety.

Having described the invention with reference to particular compositions, theories of effectiveness, and the like, it will be apparent to those of ordinary skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives therein intended, unless the context specifically indicates to the contrary.

What is claimed is:

1. A rottlerin analog comprising the following formula:

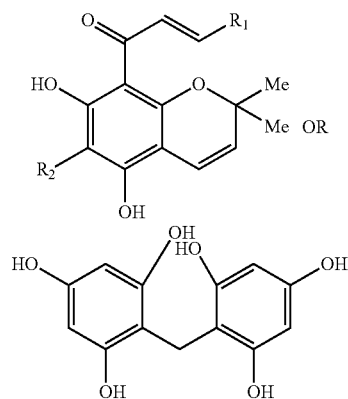

wherein R1 is selected from the group consisting of Ph (phenyl), phenol, CH$_2$Ph, CH$_2$-heterocycle and a substituted phenyl and wherein R2 is selected from the group consisting of halogens, H, OH, and benzyl, wherein said analog has biological PKCδ inhibitory potency exceeding natural rottlerin.

2. The analog of claim 1 wherein R1 is phenyl or R2 is a halogen.

3. The analog of claim 1 wherein R1 is a dihydroxy phenyl and R2 is a H.

4. The analog of claim 1 wherein R1 is a halo-phenyl and R2 is a H.

5. The analog of claim 1 wherein the phenol groups are replaced with methoxy groups.

6. A method of treating a neurological or inflammatory response mediated by protein kinase C (PKC) in an animal comprising:
  administering to an animal in need thereof, an effective amount of a rottlerin analog according to claim 1.

7. The method of claim 6 wherein said neurological or inflammatory response is Parkinson's disease.

8. A method for treating Parkinson's disease comprising:
  modulating the activity of protein kinase C δ (PKCδ) by administering a rottlerin analog according to claim 1.

9. A pharmaceutical composition for treating a neurological or inflammatory response mediated by protein kinase C (PKC) in an animal comprising:
  a rottlerin analog according to claim 1 and a pharmaceutically acceptable carrier.

* * * * *